(12) United States Patent
Brellisford et al.

(10) Patent No.: US 11,884,701 B2
(45) Date of Patent: Jan. 30, 2024

(54) CHROMATOGRAPHY MEMBRANES, DEVICES CONTAINING THEM, AND METHODS OF USE THEREOF

(71) Applicant: Merck Millipore Ltd., Carrigtwohill (IE)

(72) Inventors: Damian Brellisford, Stoney Creek (CA); Donna Lisa Crossley, Hamilton (CA); Greg McIntosh, Toronto (CA); Robert Ruman, Cambridge (CA); John Rydall, Oakville (CA); Christopher S. Shields, Windham, NH (US)

(73) Assignee: Merck Millipore Ltd., Carrigtwohill (IE)

(*) Notice: Subject to any disclaimer, the term of this patent is extended or adjusted under 35 U.S.C. 154(b) by 139 days.

(21) Appl. No.: 17/203,076

(22) Filed: Mar. 16, 2021

(65) Prior Publication Data
US 2021/0206801 A1 Jul. 8, 2021

Related U.S. Application Data

(63) Continuation of application No. 16/100,515, filed on Aug. 10, 2018, now Pat. No. 10,981,949, which is a (Continued)

(51) Int. Cl.
*C07K 1/22* (2006.01)
*B01D 63/08* (2006.01)
(Continued)

(52) U.S. Cl.
CPC .............. *C07K 1/22* (2013.01); *B01D 63/024* (2013.01); *B01D 63/034* (2022.08); (Continued)

(58) Field of Classification Search
CPC ............ B01D 2315/10; B01D 2325/36; B01D 63/02; B01D 63/024; B01D 63/082; (Continued)

(56) References Cited

U.S. PATENT DOCUMENTS 3,209,915 A 10/1965 Gutkowski
3,417,870 A 12/1968 Bray
(Continued)

FOREIGN PATENT DOCUMENTS

AU 2009288234 A1 3/2010
CA 1200158 A 2/1986
(Continued)

OTHER PUBLICATIONS

"The Water Molecule," Martin Chaplin, Apr. 3, 2001; printed from the internet on Apr. 21, 2011; <<http://xnet.rrc.mb.ca/rcharney/the%20water%20molecule.htm>>.
(Continued)

*Primary Examiner* — Dirk R Bass
(74) *Attorney, Agent, or Firm* — Foley Hoag LLP; Dana M. Gordon; Benjamin A. Vaughan

(57) ABSTRACT

Described herein are fluid treatment devices for use in tangential flow filtration, comprising a housing unit and a composite material, wherein the composite material comprises: a support member comprising a plurality of pores extending through the support member; and a non-self-supporting macroporous cross-linked gel comprising macropores having an average size of 10 nm to 3000 nm, said macroporous gel being located in the pores of the support member. The invention also relates to a method of separating a substance from a fluid, comprising the step of placing the fluid in contact with an inventive device, thereby adsorbing or absorbing the substance to the composite material contained therein.

14 Claims, 30 Drawing Sheets

Related U.S. Application Data continuation of application No. 15/427,447, filed on Feb. 8, 2017, now Pat. No. 10,800,808, which is a continuation of application No. 12/551,762, filed on Sep. 1, 2009, now abandoned.

(60) Provisional application No. 61/102,797, filed on Oct. 3, 2008, provisional application No. 61/093,600, filed on Sep. 2, 2008.

(51) Int. Cl.

| | | |
|---|---|---|
| *B01D 69/10* | (2006.01) | |
| *B01L 3/00* | (2006.01) | |
| *B01D 63/02* | (2006.01) | |
| *B01D 63/10* | (2006.01) | |
| *B01D 63/14* | (2006.01) | |
| *B01D 69/02* | (2006.01) | |
| *C07K 14/77* | (2006.01) | |
| *C07K 16/00* | (2006.01) | |
| *C12N 9/36* | (2006.01) | |
| *B01L 9/00* | (2006.01) | |

(52) U.S. Cl.
 CPC ......... *B01D 63/082* (2013.01); *B01D 63/087* (2013.01); *B01D 63/10* (2013.01); *B01D 63/14* (2013.01); *B01D 69/02* (2013.01); *B01D 69/106* (2022.08); *B01L 3/502753* (2013.01); *C07K 14/77* (2013.01); *C07K 16/00* (2013.01); *C12N 9/2462* (2013.01); *C12Y 302/01017* (2013.01); *B01D 2315/10* (2013.01); *B01D 2325/36* (2013.01); *B01L 9/527* (2013.01); *B01L 2200/0647* (2013.01); *B01L 2300/0681* (2013.01); *B01L 2300/0803* (2013.01); *B01L 2300/0816* (2013.01); *B01L 2300/0887* (2013.01); *B01L 2400/0409* (2013.01)

(58) Field of Classification Search
 CPC ...... B01D 63/087; B01D 63/10; B01D 63/14; B01D 69/02; B01D 69/10; B01L 2200/0647; B01L 2300/0681; B01L 2300/0803; B01L 2300/0816; B01L 2300/0887; B01L 2400/0409; B01L 3/502753; B01L 9/527; C07K 14/77; C07K 16/00; C07K 1/22; C12N 9/2462; C12Y 302/01017
 See application file for complete search history.

(56) References Cited

U.S. PATENT DOCUMENTS

| | | |
|---|---|---|
| 3,473,668 A | 10/1969 | Bunyard et al. |
| 3,623,610 A | 11/1971 | Olsen et al. |
| 3,695,444 A | 10/1972 | Iaconelli |
| 3,713,921 A | 1/1973 | Fleischer et al. |
| 3,875,085 A | 4/1975 | Bolto |
| 3,933,646 A | 1/1976 | Kanamaru et al. |
| 3,939,105 A | 2/1976 | Jones, Jr. et al. |
| 3,997,482 A | 12/1976 | Turkova et al. |
| 4,104,125 A | 8/1978 | Takechi et al. |
| 4,108,804 A | 8/1978 | Seita et al. |
| 4,133,764 A | 1/1979 | Bardin et al. |
| 4,170,540 A | 10/1979 | Lazarz et al. |
| 4,198,238 A | 4/1980 | Scheve |
| 4,224,415 A | 9/1980 | Meitzner et al. |
| 4,230,697 A | 10/1980 | Nishida et al. |
| 4,275,056 A | 6/1981 | Takaku et al. |
| 4,377,481 A | 3/1983 | Jakabhazy |
| 4,381,775 A | 5/1983 | Nose et al. |
| 4,397,892 A | 8/1983 | Lorant et al. |
| 4,473,474 A | 9/1984 | Ostreicher et al. |
| 4,504,583 A | 3/1985 | Hasegawa et al. |
| 4,518,695 A | 5/1985 | Hasegawa |
| 4,525,374 A | 6/1985 | Vaillancourt |
| 4,525,527 A | 6/1985 | Takeda et al. |
| 4,601,828 A | 7/1986 | Gershoni |
| 4,678,844 A | 7/1987 | Sakuragi et al. |
| 4,705,755 A | 11/1987 | Hasegawa et al. |
| 4,790,942 A | 12/1988 | Shmidt et al. |
| 4,814,077 A | 3/1989 | Furuyoshi et al. |
| 4,836,928 A | 6/1989 | Aoyagi et al. |
| 4,888,116 A | 12/1989 | Cadotte et al. |
| 4,889,632 A | 12/1989 | Svec et al. |
| 4,897,191 A | 1/1990 | Langerak et al. |
| 4,923,610 A | 5/1990 | Svec et al. |
| 4,944,879 A | 7/1990 | Steuck |
| 4,952,349 A | 8/1990 | Svec et al. |
| 4,966,851 A | 10/1990 | Durance et al. |
| 4,969,997 A | 11/1990 | Kluver et al. |
| 4,999,171 A | 3/1991 | Kato et al. |
| 5,019,139 A | 5/1991 | LaPack et al. |
| 5,019,270 A | 5/1991 | Afeyan et al. |
| 5,059,659 A | 10/1991 | Gregor et al. |
| 5,100,549 A | 3/1992 | Langerak et al. |
| 5,114,582 A | 5/1992 | Sandstrom et al. |
| 5,114,585 A | 5/1992 | Kraus et al. |
| 5,122,558 A | 6/1992 | Knobel et al. |
| 5,130,343 A | 7/1992 | Frechet et al. |
| 5,137,633 A | 8/1992 | Wang |
| 5,143,616 A | 9/1992 | Pall et al. |
| 5,147,541 A | 9/1992 | McDermott, Jr. et al. |
| 5,160,627 A | 11/1992 | Cussler et al. |
| 5,176,832 A | 1/1993 | Dorta et al. |
| 5,192,678 A | 3/1993 | Iwami et al. |
| 5,211,728 A | 5/1993 | Trimmer |
| 5,221,477 A | 6/1993 | Melcher et al. |
| 5,225,120 A | 7/1993 | Graiver et al. |
| 5,227,063 A | 7/1993 | Langerak et al. |
| 5,228,989 A | 7/1993 | Afeyan et al. |
| 5,232,593 A | 8/1993 | Pedersen et al. |
| 5,268,306 A | 12/1993 | Berger et al. |
| 5,269,931 A | 12/1993 | Hu et al. |
| 5,277,915 A | 1/1994 | Provonchee et al. |
| 5,282,971 A | 2/1994 | Degen et al. |
| 5,284,584 A | 2/1994 | Huang et al. |
| 5,316,680 A | 5/1994 | Frechet et al. |
| 5,317,932 A | 6/1994 | Westlake, III et al. |
| 5,334,310 A | 8/1994 | Frechet et al. |
| 5,384,042 A | 1/1995 | Afeyan et al. |
| 5,403,482 A | 4/1995 | Steere et al. |
| 5,409,515 A | 4/1995 | Yamamoto et al. |
| 5,422,284 A | 6/1995 | Lau |
| 5,433,861 A | 7/1995 | Frawley et al. |
| 5,460,720 A | 10/1995 | Schneider |
| 5,470,469 A | 11/1995 | Eckman |
| 5,472,606 A | 12/1995 | Steere et al. |
| 5,562,827 A | 10/1996 | Schmidt et al. |
| 5,593,576 A | 1/1997 | Girot et al. |
| 5,593,729 A | 1/1997 | Frechet et al. |
| 5,599,453 A | 2/1997 | Girot et al. |
| 5,607,586 A | 3/1997 | Grangeon et al. |
| 5,646,001 A | 7/1997 | Terstappen et al. |
| 5,647,979 A | 7/1997 | Liao et al. |
| 5,648,390 A | 7/1997 | Vander Meer et al. |
| 5,672,276 A | 9/1997 | Girot et al. |
| 5,681,464 A | 10/1997 | Larsson |
| 5,695,653 A | 12/1997 | Gsell et al. |
| 5,723,601 A | 3/1998 | Larsson et al. |
| 5,728,457 A | 3/1998 | Frechet et al. |
| 5,733,452 A | 3/1998 | Whitlock |
| 5,739,190 A | 4/1998 | Hartmann et al. |
| 5,756,717 A | 5/1998 | Paliwal et al. |
| 5,762,789 A | 6/1998 | de los Reyes et al. |
| 5,780,688 A | 7/1998 | Hoffmann et al. |
| 5,783,085 A | 7/1998 | Fischel |
| 5,833,860 A | 11/1998 | Kopaciewicz et al. |
| 5,897,779 A | 4/1999 | Wisted et al. |
| 5,906,734 A | 5/1999 | Girot et al. |
| 5,929,214 A | 7/1999 | Peters et al. |

(56) References Cited

U.S. PATENT DOCUMENTS

| | | |
|---|---|---|
| 5,972,634 A | 10/1999 | Tanzi et al. |
| 5,976,380 A | 11/1999 | Moya |
| 6,033,784 A | 3/2000 | Jacobsen et al. |
| 6,045,697 A | 4/2000 | Girot et al. |
| 6,086,769 A | 7/2000 | Kilambi et al. |
| 6,103,119 A | 8/2000 | Clements et al. |
| 6,143,174 A | 11/2000 | Graus et al. |
| 6,153,098 A | 11/2000 | Bayerlein et al. |
| 6,186,341 B1 | 2/2001 | Konstantin et al. |
| 6,190,557 B1 | 2/2001 | Hisada et al. |
| 6,207,806 B1 | 3/2001 | Brierley et al. |
| 6,258,276 B1 | 7/2001 | Mika et al. |
| 6,271,278 B1 | 8/2001 | Park et al. |
| 6,277,489 B1 | 8/2001 | Abbott et al. |
| 6,331,253 B1 | 12/2001 | Schrive et al. |
| 6,387,271 B1 | 5/2002 | Geibel et al. |
| 6,391,200 B2 | 5/2002 | Pulek et al. |
| 6,454,942 B1 | 9/2002 | Shintani et al. |
| 6,461,513 B1 | 10/2002 | Jen |
| 6,461,517 B1 | 10/2002 | Miwa et al. |
| 6,468,657 B1 | 10/2002 | Hou et al. |
| 6,475,071 B1 | 11/2002 | Joslyn |
| 6,494,936 B1 | 12/2002 | Peacock |
| 6,495,041 B2 | 12/2002 | Taniguchi et al. |
| 6,613,234 B2 | 9/2003 | Voute et al. |
| 6,623,631 B1 | 9/2003 | Graus et al. |
| 6,635,104 B2 | 10/2003 | Komkova et al. |
| 6,635,420 B1 | 10/2003 | Hosel et al. |
| 6,709,598 B1 | 3/2004 | Pearl |
| 6,766,817 B2 | 7/2004 | da Silva et al. |
| 6,780,327 B1 | 8/2004 | Wu et al. |
| 6,780,582 B1 | 8/2004 | Wagner et al. |
| 6,824,679 B1 | 11/2004 | Dzengeleski et al. |
| 6,824,975 B2 | 11/2004 | Hubscher et al. |
| 6,851,561 B2 | 2/2005 | Wu et al. |
| 6,884,345 B1 | 4/2005 | Irgum et al. |
| 6,887,384 B1 | 5/2005 | Frechet et al. |
| 6,902,671 B2 | 6/2005 | Cappia et al. |
| 6,911,148 B1 | 6/2005 | Demmer et al. |
| 6,913,786 B2 | 7/2005 | Proulx et al. |
| 6,918,404 B2 | 7/2005 | Dias da Silva et al. |
| 6,926,823 B2 | 8/2005 | Kallury et al. |
| 6,951,880 B2 | 10/2005 | Roberts et al. |
| 6,953,686 B1 | 10/2005 | Ramasubramanyan |
| 6,984,604 B2 | 1/2006 | Cobb et al. |
| 6,986,847 B2 | 1/2006 | Sirkar et al. |
| 7,048,855 B2 | 5/2006 | de la Cruz |
| 7,066,586 B2 | 6/2006 | da Silva et al. |
| 7,073,671 B2 | 7/2006 | Charkoudian |
| 7,094,347 B2 | 8/2006 | Wu et al. |
| 7,163,803 B2 | 1/2007 | Hamon et al. |
| 7,189,771 B2 | 3/2007 | Hsu |
| 7,247,370 B2 | 7/2007 | Childs et al. |
| 7,284,668 B2 | 10/2007 | Charkoudian |
| 7,285,255 B2 | 10/2007 | Kadlec et al. |
| 7,316,919 B2 | 1/2008 | Childs et al. |
| 7,351,335 B2 | 4/2008 | Broens et al. |
| 7,410,581 B2 | 8/2008 | Arnold et al. |
| 7,452,697 B2 | 11/2008 | Luo et al. |
| 7,504,034 B2 | 3/2009 | Minegishi et al. |
| 7,507,420 B2 | 3/2009 | Ng et al. |
| 7,598,371 B2 | 10/2009 | Willson et al. |
| 7,736,504 B2 | 6/2010 | Fritze et al. |
| 7,824,548 B2 | 11/2010 | DiLeo et al. |
| 7,879,758 B2 | 2/2011 | Heidenreich et al. |
| 7,883,767 B2 | 2/2011 | Childs et al. |
| 8,110,525 B2 | 2/2012 | Xiao et al. |
| 8,206,958 B2 | 6/2012 | Childs et al. |
| 8,211,682 B2 | 7/2012 | Childs et al. |
| 8,383,782 B2 | 2/2013 | Childs et al. |
| 9,873,088 B2 | 1/2018 | Kanani et al. |
| 10,195,567 B2 | 2/2019 | Kanani et al. |
| 10,800,808 B2 | 10/2020 | Brellisford et al. |
| 10,874,990 B2 | 12/2020 | Kanani et al. |
| 10,981,949 B2 | 4/2021 | Brellisford et al. |
| 2001/0037982 A1 | 11/2001 | Pulek et al. |
| 2002/0005383 A1 | 1/2002 | Voute et al. |
| 2002/0148769 A1 | 10/2002 | Deuschle et al. |
| 2003/0000890 A1 | 1/2003 | Quick et al. |
| 2003/0006186 A1 | 1/2003 | Pulek et al. |
| 2003/0047504 A1* | 3/2003 | Scheper ............ B01J 20/28057 210/295 |
| 2003/0155243 A1 | 8/2003 | Sferrazza |
| 2003/0155290 A1 | 8/2003 | Chanaud |
| 2003/0232895 A1 | 12/2003 | Omidian et al. |
| 2004/0195164 A1 | 10/2004 | Hirokawa et al. |
| 2004/0203149 A1 | 10/2004 | Childs et al. |
| 2005/0133424 A1 | 6/2005 | Bouvier et al. |
| 2006/0175256 A1 | 8/2006 | Masten et al. |
| 2007/0212281 A1 | 9/2007 | Kadlec et al. |
| 2008/0017578 A1 | 1/2008 | Childs et al. |
| 2008/0035558 A1 | 2/2008 | Shah |
| 2008/0156718 A1 | 7/2008 | Larsen |
| 2008/0190836 A1 | 8/2008 | Beppu et al. |
| 2008/0230488 A1 | 9/2008 | Gutman et al. |
| 2008/0264867 A1 | 10/2008 | Mika et al. |
| 2008/0312416 A1 | 12/2008 | Childs et al. |
| 2008/0314831 A1 | 12/2008 | Childs et al. |
| 2009/0107922 A1 | 4/2009 | Zhang et al. |
| 2009/0200226 A1 | 8/2009 | Straeffer et al. |
| 2010/0059443 A1 | 3/2010 | Brellisford et al. |
| 2011/0006007 A1 | 1/2011 | Kuruc et al. |
| 2011/0030382 A1 | 2/2011 | Eadon et al. |
| 2011/0049042 A1 | 3/2011 | DiLeo et al. |
| 2017/0145053 A1 | 5/2017 | Brellisford et al. |
| 2018/0141004 A1 | 5/2018 | Kanani et al. |

FOREIGN PATENT DOCUMENTS

| | | |
|---|---|---|
| CA | 2054933 A1 | 6/1992 |
| CA | 2173754 A1 | 4/1995 |
| CA | 2428280 | 5/2002 |
| CA | 2736814 C | 2/2017 |
| DE | 3918439 A1 | 12/1989 |
| DE | 39 18 430 A1 | 12/1990 |
| DE | 195 40 876 A1 | 5/1997 |
| DE | 199 43 921 | 1/2001 |
| EP | 105629 A2 | 4/1984 |
| EP | 0163146 A1 | 12/1985 |
| EP | 0304161 A2 | 2/1989 |
| EP | 0316642 A2 | 5/1989 |
| EP | 327025 A1 | 8/1989 |
| EP | 343895 A2 | 11/1989 |
| EP | 0369769 A2 | 5/1990 |
| EP | 0506247 A2 | 9/1992 |
| EP | 0581544 A2 | 2/1994 |
| EP | 610755 A1 | 8/1994 |
| EP | 0320023 B1 | 9/1994 |
| EP | 662340 A1 | 7/1995 |
| EP | 0664732 B1 | 12/1997 |
| EP | 907397 A1 | 4/1999 |
| EP | 942251 A2 | 9/1999 |
| EP | 1017470 A1 | 7/2000 |
| EP | 1146944 A2 | 10/2001 |
| EP | 1163036 A1 | 12/2001 |
| EP | 1286745 A1 | 3/2003 |
| EP | 1286755 A1 | 3/2003 |
| EP | 1311333 A1 | 5/2003 |
| EP | 1323461 A2 | 7/2003 |
| EP | 1364080 A2 | 11/2003 |
| EP | 1405828 A1 | 4/2004 |
| EP | 1453593 A1 | 9/2004 |
| EP | 1554028 A1 | 7/2005 |
| EP | 1570898 A1 | 9/2005 |
| EP | 1609522 A2 | 12/2005 |
| EP | 1736233 A1 | 12/2006 |
| EP | 1849516 A1 | 10/2007 |
| EP | 2 143 481 A1 | 1/2010 |
| EP | 2334413 A2 | 6/2011 |
| EP | 2334413 A4 | 6/2011 |
| JP | S61-163004 U | 10/1986 |
| JP | 62014903 | 1/1987 |
| JP | S6239636 A | 2/1987 |
| JP | S62-258702 A | 11/1987 |

(56) References Cited

FOREIGN PATENT DOCUMENTS

| | | |
|---|---|---|
| JP | H01070108 U | 5/1989 |
| JP | H010180048 A | 7/1989 |
| JP | H03143532 A | 6/1991 |
| JP | H06047259 A | 2/1994 |
| JP | 06100725 A | 4/1994 |
| JP | H08024598 A | 1/1996 |
| JP | H0852329 A | 2/1996 |
| JP | H08206474 A | 8/1996 |
| JP | H08281083 A | 10/1996 |
| JP | H8281084 A | 10/1996 |
| JP | H08295630 A | 11/1996 |
| JP | H0947639 A | 2/1997 |
| JP | H0999223 A | 4/1997 |
| JP | H09103661 A | 4/1997 |
| JP | H09119684 A | 5/1997 |
| JP | H1076144 A | 3/1998 |
| JP | H10057780 A | 3/1998 |
| JP | 11033370 | 2/1999 |
| JP | H1157703 A | 3/1999 |
| JP | 2000070683 A | 3/2000 |
| JP | 2000246067 A | 9/2000 |
| JP | 2000291988 A | 10/2000 |
| JP | 2001038155 A | 2/2001 |
| JP | 2001038157 A | 2/2001 |
| JP | 2001038158 A | 2/2001 |
| JP | 2001146404 A | 5/2001 |
| JP | 2001293337 A | 10/2001 |
| JP | 2002-166146 A | 6/2002 |
| JP | 2002186839 A | 7/2002 |
| JP | 2002248324 A | 9/2002 |
| JP | 2002273181 A | 9/2002 |
| JP | 2003144863 A | 5/2003 |
| JP | 2003225661 A | 8/2003 |
| JP | 2003251386 A | 9/2003 |
| JP | 2003326139 A | 11/2003 |
| JP | 2003326140 A | 11/2003 |
| JP | 2004067402 A | 3/2004 |
| JP | 2004089761 A | 3/2004 |
| JP | 2005211819 A | 8/2005 |
| JP | 2006021129 A | 1/2006 |
| JP | 2006102662 A | 4/2006 |
| JP | 2006150239 A | 6/2006 |
| JP | 2006/519273 A | 8/2006 |
| JP | 2007111674 A | 5/2007 |
| JP | 2007136349 A | 6/2007 |
| JP | 2007253089 A | 10/2007 |
| JP | 2007313389 A | 12/2007 |
| JP | 2007313390 A | 12/2007 |
| JP | 2012501245 A | 1/2012 |
| JP | 5146647 B2 | 2/2013 |
| KR | 100236921 B1 | 1/2000 |
| KR | 20050107440 A | 11/2005 |
| KR | 1020080016740 A | 2/2008 |
| KR | 20090033518 A | 4/2009 |
| KR | 1020090033518 | 4/2009 |
| RU | 2236382 C2 | 9/2004 |
| WO | WO-87/06395 A1 | 10/1987 |
| WO | WO-90/04609 | 5/1990 |
| WO | WO-91/00762 | 1/1991 |
| WO | WO-91/14076 | 9/1991 |
| WO | WO-92/05595 A1 | 4/1992 |
| WO | WO-92/07899 | 5/1992 |
| WO | WO-93/07945 | 4/1993 |
| WO | WO-93/19115 A1 | 9/1993 |
| WO | WO-94/08686 A1 | 4/1994 |
| WO | WO-94/08713 | 4/1994 |
| WO | WO-94/09063 | 4/1994 |
| WO | WO-95/10346 | 4/1995 |
| WO | WO-97/17129 | 5/1997 |
| WO | WO-97/18904 | 5/1997 |
| WO | WO-97/019744 A1 | 6/1997 |
| WO | WO-98/00220 A1 | 1/1998 |
| WO | WO-98/01208 | 1/1998 |
| WO | WO-98/17377 | 4/1998 |
| WO | WO-98/35738 A1 | 8/1998 |
| WO | WO-99/13958 | 3/1999 |
| WO | WO-99/20378 | 4/1999 |
| WO | WO-00/12618 A1 | 3/2000 |
| WO | WO-00/13767 A1 | 3/2000 |
| WO | WO-2000/029098 A1 | 5/2000 |
| WO | WO-00/44485 | 8/2000 |
| WO | WO-00/50160 A1 | 8/2000 |
| WO | WO-00/50161 | 8/2000 |
| WO | WO-00/54866 | 9/2000 |
| WO | WO-00/69549 | 11/2000 |
| WO | WO-01/08792 A2 | 2/2001 |
| WO | WO-01/092607 A1 | 12/2001 |
| WO | WO-01/93980 | 12/2001 |
| WO | WO-02/05924 A1 | 1/2002 |
| WO | WO-02/05934 A2 | 1/2002 |
| WO | WO-02/16675 A2 | 2/2002 |
| WO | WO-02/28947 | 4/2002 |
| WO | WO-02/38257 | 5/2002 |
| WO | WO-02/096538 A1 | 12/2002 |
| WO | WO-03/008078 A2 | 1/2003 |
| WO | WO-03/049842 | 6/2003 |
| WO | WO-2004/009201 A2 | 1/2004 |
| WO | WO-2004/028660 | 4/2004 |
| WO | WO-2004/073843 A1 | 9/2004 |
| WO | WO-2004/110132 A2 | 12/2004 |
| WO | WO-2005037917 A1 | 4/2005 |
| WO | WO-2005/097304 | 10/2005 |
| WO | WO-2005118106 A2 * | 12/2005 ......... B01D 19/0031 |
| WO | WO-2006/015495 | 2/2006 |
| WO | WO-2006/091167 A1 | 8/2006 |
| WO | WO-2007/038542 A2 | 4/2007 |
| WO | WO-2007/110203 A1 | 10/2007 |
| WO | WO-2010/027955 A2 | 3/2010 |
| WO | WO-2010/062454 A1 | 6/2010 |
| WO | WO-2010027955 A3 | 6/2010 |
| WO | WO-2010/117598 A2 | 10/2010 |
| WO | WO-2010/129171 A2 | 11/2010 |
| WO | WO-11/025698 A1 | 3/2011 |

OTHER PUBLICATIONS

Afeyan, N.B. et al., "Flow-through particles for the high-performance liquid chromatographic separation of biomolecules: perfusion chromatography," J Chromatogr, 519:1-29 (1990).

Akhtar, S. et al., "Coatings reduce the fouling of microfiltration membranes," J Memb Sci, 107:209-18 (1995).

Alpert, A.J. et al., "Preparation of a Porous Microparticulate Anion-Exchange Chromatography Support for Proteins," J Chrom, 185:375-92 (1979).

Altomare, A. et al., "Methacrylic polymers containing permanent dipole azobenzene chromophores spaced from from the main chain. 13C NMR spectra and photochromic properties," Macromol Chem Phys, 200:601-8 (1999).

Altomare, A. et al., "Synthesis and polymerization of amphiphilic methacrylates containing permanent dipole azobenzene chromophores," J Polym Sci Pol Chem, 39:2957-77 (2001).

Anderson, J.L. et al., "Model for Hydrodynamic Thickness of Thin Polymer Layers at Solid/Liquid Interfaces," Langmuir, 7:162-6 (1991).

Arshady, R., "In the name of particle formation," Colloid Surface A, 153:325-33 (1999).

Barbucci, R. et al., "Synthesis, chemical and rehological characterization of new hyaluronic acid-based hydrogels," J Biomater Sci-Polymer Edn, 11:383-99 (2000).

Barton, A.F.M., CRC Handbook of Solubility Parameters and Other Cohesion Parameters, 2nd Ed., CRC Press, Boca Raton, FL, Chapter 14, pp. 405-464 (1991).

Boschetti, E., "Advanced sorbents for preparative protein separation purposes," J Chromatogr A, 658:207-36 (1994).

Brandrup et al. (edited by), Polymer Handbook Chapter VII, Wiley and Sons, New York (1999).

Cabasso, I. et al., "Composite Hollow Fiber Membranes," J Appl Polym Sci, 23:1509-25 (1979).

Chanda, M. et al., "A new method of gel-coating polyethyleneimine (PEI) on organic resin beads. High capacity and fast kinetics of PEI gel-coated on polystyrene," Ind Eng Chem Res, 40:1624-32 (2001).

(56) References Cited

OTHER PUBLICATIONS

Charcosset, C., "Purification of proteins by membrane chromatography," J Chem Technol Biot, 71:95-110 (1998).
Chen et al., "Comparison of standard and new generation hydrophobic interaction chromatography resins in the monoclonal antibody purification process," Journal of Chromatography A, 1177:272-281 (2008).
Childs, R.F. et al., "Formation of pore-filled microfiltration membranes using a combination of modified interfacial polymerization and grafting," J Polym Sci Pol Chem, 40:242-50 (2002).
Childs, R.F., et al., The design of high performance, gel-filled nanofiltration membranes, in a New Insights into Membrane Science and Technology: Polymeric, Inorganic and Biofunctional Membranes@ Elsevier, Edit. A Butterfield and D Bhattacharyya, (2003) p. 353-375.
Choi et al., "Separation of proteins on polymeric stationary phases grafted with various amine groups" J Chromatogr A, 987: 323-330 (2003).
Claesson, P.M. et al., "Adsorption and interaction of a graft copolymer of poly(ethylene imine) and poly(ethylene oxide)," Colloid Surface, 112:131-9 (1996).
Claesson, P.M. et al., "Surface properties of poly(ethylene imine)-coated mica surfaces—salt and pH effects," Colloid Surface, 123-124:341-53 (1997).
Dickson, J.M. et al., "Development of a coating technique for the internal structure of polypropylene microfiltration membranes," J Membrane Sci, 148:25-36 (1998).
Diogo et al., "Purification of a Cystic Fibrosis Plasmid Vector for Gene Therapy Using Hydrophobic Interaction Chromatography," Biotechnology Bioengineering, 68(5):576-583 (2000).
Donald, "Environmental scanning electron microscopy for the study of 'wet' systems," Current Opinion in Colloid & Interface Science, 3(2):143-147 (1998).
Dudley, L.Y. et al., "Coatings for the prevention of fouling of microfiltration membranes," Chem Eng Res Des, 71 (part A):327-8 (1993).
Eisenbach, C.D., "Isomerization of aromatic azo chromophores in poly(ethyl acrylate) networks and photomechanical effect," Polymer, 21:1175-9 (1980).
Erim, F.B. et al., "Performance of a physically adsorbed high-molecular-mass polyethyleneimine layer as coating for the separation of basic proteins and peptides by capillary electrophoresis," J Chromatogr, 708:356-61 (1995).
Erim, F.B., "Separation of phenols by capillary electrophoresis in a polyethylenemine-coated capillary," Microchem J, 57:283-7 (1997).
European Search Report dated Apr. 7, 2009 from 05 732 196.0.
European Search Report dated Nov. 17, 2009 from EP 09 17 2742.0.
European Search Report dated Nov. 18, 2009 from EP 09 17 2746.1.
Extended European Search Report for EP Application No. 18187060.1-1104/3427815 dated Dec. 19, 2018.
Ghosh, R. et al., "Analysis of protein transport and polarization through membranes using pulsed sample injection technique," J Membrane Sci, 175:75-84 (2000).
Ghosh, R. et al., "Parameter scanning ultrafiltration: rapid optimisation of protein separation," Biotechnol Bioeng, 81:673-82 (2003).
Ghosh, R., "Bioseparation using supported liquid membrane chromatography," J Membrane Sci, 192:243-7 (2001).
Ghosh, R., "Fractionation of biological macromolecules using carrier phase ultrafiltration," Biotechnol Bioeng, 74(1):1-11 (2001).
Ghosh, R., "Protein separation using membrane chromatography: opportunities and challenges," J Chromatogr, 952:13-27 (2002).
Grulke, E.A., Polymer Handbook, 4th Ed. (1999), Brandrup, J., et al., Wiley-Interscience, New York, Chapter VII, pp. 675, 697 and 711.
Happel et al., "Low Reynolds No. hydrodynamics," Noordhoff Int Publ, Leyden, p. 393 (1973).
Hatch et al., "Preparation and use of snake-cage polyelectrolytes," Ind Eng Chem, 49:1812-9 (1957).
Hoffer, E. et al., "Hyperfiltration in charged membranes: the fixed charge model," Desalination, 13:1280-90 (1967).
Horie et al., "Definitions of terms relating to reactions of polymers and to functional polymeric materials," Pure Appl Chem, 76(4):889-906 (2004).
Hvid, K.B. et al., "Preparation and characterization of a new ultrafiltration membrane," J Membrane Sci, 53:189-202 (1990).
Hydrophobic Interaction Chromatography, Principles and Methods, Amersham Pharmacia Biotech, Ed. AB, pp. 1-104 (1993).
Idol, W.K. et al., "Effects of adsorbed polyelectrolytes on convective flow and diffusion in porous membranes," J Memb Sci, 28:269-86 (1986).
Iki et al., "A New Chiral Stationary Phase for Gas Chromatography by Use of a Chiral Thiacalix[4]arene Derivative," Chemistry Letters, 27(10):1065-1066 (1998).
International Search Report dated Apr. 16, 2010 from PCT/US2009/055582.
International Search Report dated Apr. 4, 2011 from PCT/IB2010/003049.
International Search Report dated Aug. 5, 2005 (dated Aug. 23, 2005) from PCT/CA05/000880.
International Search Report dated Feb. 1, 2013 from PCT/US2012/038318.
International Search Report dated Jun. 21, 2005 (dated Jul. 20, 2005) from PCT/CA05/000518.
International Search Report dated Sep. 18, 2014, from PCT/IB2014/001022.
International Search Report for PCT/US2011/051364 dated Apr. 26, 2012.
Inukai, M. et al., "Preparation and characterization of hyaluronate—hydroxyethyl acrylate blend hydrogel for controlled release device," Chem Pharm Bull, 48:850-4 (2000).
Iritani et al., "Concentration of proteinaceous solutions with superabsorbent hydrogels," Separ Sci Technol, 28(10):1819-1836 (1993).
IUPAC Compendium of Chemical Terminology, "Macroporour polymer," PAC, (2014).
Jacobsen, C. et al., "Soft x-ray spectroscopy from image sequences with sub-100 nm spatial resolution," J Microsc, 197(Pt 2):173-84 (2000).
Jensen, M. et al., "Loading into and electro-stimulated release of peptides and proteins from chondroitin 4-sulphate hydrogels," Eur J Pharm Sci, 15:139-48 (2002).
Ji, Chun-Nuan, et al.; "Studies on synthesis and properties of snake—cage type chelating resin of carboxymethyl cellulose-ethylenediamine-B-62", XP002522863 retrieved from STN Database accession No. 2003:314324 (abstract) & Linchan Huaxue Yu Gongye, 23(1), 35-38 Coden: LHYGD7; Issn: 0253-2417, 2003.
Jiang, W. et al., "Pore-filled cation-exchange membranes containing poly(styrenesulfonic acid) gels," Desalination, 159:253-66 (2003).
Kabra et al., "Synthesis of fast response, temperature-sensitive poly (N-isopropylacrylamide) gel," Polymer Communications, 32(11):322-323 (1991).
Kagatani, S. et al., "Electroresponsive pulsatile depot delivery of insulin from poly(dimethylaminopropylacrylamide) gel in rats," J Pharm Sci, 86(11):1273-7 (1997).
Kapur et al., "Hydrodynamic permeability of hydrogels stabilized within porous membranes," Ind Eng Chem Res, 35:3179-3185 (1996).
Kapur, V., "Transport in polymer/gel-modified micropores," Ph.D. Thesis, Carnegie-Mellon University, 56:229 (1996).
Kato et al., "Hydrophobic interaction chromatography at low salt concentration for the capture of monoclonal antibodies," Journal of Chromatography A, 1036:45-50 (2004).
Kawai, T. et al., "Extension and shrinkage of polymer brush grafted onto porous membrane induced by protein binding," Macromolecules, 33:1306-9 (2000).
Kim, J.H. et al., "Rapid temperature/pH response of porous alginate-g-poly(N-isopropylacrylamide) hydrogels," Polymer, 43:7549-58 (2002).
Kim, J.T. et al., "Diffusion and flow through polymer-lined micropores," Ind Eng Chem Res, 30:1008-16 (1991).
Kim, J.T. et al., "Hindered transport through micropores with adsorbed polyelectrolytes," J Membrane Sci, 47:163-82 (1989).

(56) References Cited

OTHER PUBLICATIONS

Koehler et al., "Enhancing Protein A performance in mAb processing: A method to reduce and rapidly evaluate host cell DNA levels during primary clarification," Biotechnology Progress, 35: e2882 (2019).
Konitturi, K. et al., "Modeling of the salt and pH effects on the permeability of grafted porous membranes," Macromolecules, 29:5740-6 (1996).
Kumar, G.S. et al., "Chelating copolymers containing photosensitive functionalities. 3. Photochromism of cross-linked polymers," Macromolecules, 18(8): 1525-30 (1985).
Li et al., "Rapid chiral separation by flow-through chromatography with a biporous stationary phase," Chromatographia, 61: 213-217 (2005).
Liu et al., "Recovery and purification process development for monoclonal antibody production," MAbs, 2(5): 480-499 (2010).
Liu, H.C. et al., "Breakthrough of lysozyme through an affinity membrane of cellulose-cibacrom blue," AIChE J, 40:40-9 (1994).
Liu, Q. et al., "Preparation of macroporous poly(2-hydroxyethyl methacrylate) hydrogels by enhanced phase separation" (2000) Biomaterials, 21, p. 2163-2169.
Lozinsky, V. et al., "The potential of polymeric cryogels in bioseparation," Bioseparation, 10:163-88 (2002).
Ma et al., "Covalent immobilization of albumin on micron-sized magnetic poly(methyl methacrylate-divinylbenzene-glycidyl methacrylate) microspheres prepared by modified suspension polymerization," Polymers for Advanced Technologies, 16(7), 554-558 (2005).
Mallik et al., "High-Performance Affinity Monolith Chromatography: Development and Evaluation of Human Serum Albumin Columns," Analytical Chemistry, 76(23): 7013-7022 (2004).
McNeff, C. et al., "High-performance anion exchange of small anions with polyethyleneimine-coated porous zirconia," J Chromatogr A, 684:201-11 (1994).
Merhar et al., "Methacrylate monoliths prepared from various hydrophobic and hydrophilic monomers—Structural and chromatographic characteristics," Journal of Separation Science, 26:322-330 (2003).
Mika et al., "Calculation of the hydrodynamic permeability of gels and gel-filled microporous membranes," Ind Eng Chem Res, 40:1694-1705 (2001).
Mika, A.M. et al., "A new class of polyelectrolyte-filled microfiltration membranes with environmentally controlled porosity," J Membrane Sci, 108:37-56 (1995).
Mika, A.M. et al., "Acid/base properties of poly(4-vinylpyridine) anchored within microporous membranes," J Membrane Sci, 152:129-40 (1998).
Mika, A.M. et al., "Chemical valves based on poly(4-vinylpyridine)-filled microporous membrane," J Membrane Sci, 153:45-56 (1999).
Mika, A.M. et al., "Poly(4-vinylpyridine)-filled microfiltration membranes: physicochemical properties and morphology," J Membrane Sci, 136:221-32 (1997).
Mika, A.M. et al., "Porous, polyelectrolyte-filled membranes: effect of cross-linking on flux and separation," J Membrane Sci, 135:81-92 (1997).
Mika, A.M. et al., "Salt separation and hydrodynamic permeability of a porous membrane filled with pH-sensitive gel," J Membrane Sci, 206:19-30 (2002).
Mika, A.M. et al., "Ultra-low pressure water softening with pore-filled membranes," Desalination, 140:265-75 (2001).
Mika, A.M. et al., "Ultra-low pressure water softening: a new approach to membrane construction," Desalination, 121:149-58 (1999).
Murakami, R. et al., "Properties of poly(vinyl alcohol)/silica hybrid gel particles," J Mater Sci Lett, 14:937-8 (1995).
Murdan, S. et al., "Electro-responsive drug delivery from hydrogels," J Control Release, 92:1-17 (2003).
Nagaoka, S., "Mechanical properties of composite hydrogels," Polym J, 21:847-50 (1989).
Nakamura et al., "Chiral separation of dl-tryptophan using porous membranes containing multilayered bovine serum albumin cross-linked with glutaraldehyde," J Chromatogr A, 822(1): 53-58 (1998).
Nakanishi, K. et al., "Porous gel coatings obtained by phase separation in ORMOSIL system," Mater Res Soc Symp Proc, 628:CC7.6.1-CC7.6.11 (2000).
Okano et al., "Intelligent biointerface: remote control for hydrophilic-hydrophobic property of the material surfaces by temperature," presented at the Third ICIM/ECSSM '96, Lyon '96, pp. 34-41.
Okay, "Macroporous copolymer networks," Prog Polym Sci, 25:711-779 (2000).
Oxley, H.R. et al., "Macroporous hydrogels for biomedical applications: methodology and morphology," (1993) Biomaterials, 14(14):1064-72 (1993).
Padmavathi et al., "Structural characteristics and swelling behavior of poly(ethylene glycol) diacrylate hydrogels," Macromolecules, 29:1976-9 (1996).
Pandey, A.K. et al., "Formation of pore-filled ion-exchange membranes with in-situ crosslinking: poly(vinylbenzyl ammonium salt)-filled membranes," J Polym Sci Pol Chem, 39:807-20 (2001).
Park et al., "Estimation of Temperature-Dependent Pore Size in Poly(N-isopropylacrylamide) Hydrogel Beads," Biotechnology Prog., 10:82-86 (1994).
Petsch, D. et al., "Selective adsorption of endotoxin inside a polycationic network of flat-sheet microfiltration membranes," J Mol Recognit, 11:222-30 (1998).
Rabelo et al., "Structure and properties of styrene-divinylbenzene copolymers," Polym Bull, 33:479, 487 and 493 (1994).
Righetti, "Macroporous gels: facts and misfacts," Journal of Chromatography, 698:3-17 (1995).
Roque, A.C.A. et al., "Affinity-based methodologies and ligands for antibody purification: advances and perspectives," J Chromatogr A, 1160:44-55 (2007).
Rounds, M.A. et al., "Poly(styrene-divinylbenzene)-based strong anion-exchange packing material for high-performance liquid chromatography of proteins," J Chromatogr, 397:25-38 (1987).
Saito, K., "Charged polymer brush grafted onto porous hollow-fiber membrane improves separation and reaction in biotechnology," Separ Sci Technol, 37(3):535-554 (2002).
Sata, T. et al., "Modification of properties of ion exchange membranes," Coll Sci, 256:757-69 (1978).
Schaefer, D.W. et al., "Dynamics of semiflexible polymers in solution," Macromolecules, 13:1280-90 (1980).
Smets, G. et al., "Chemical reactions in solid polymeric systems. Photomechanical phenomena," Pure Appl Chem, 39:225-38 (1974).
Smets, G. et al., "Photochromic phenomena in the solid phase," Adv Polym Sci, 50:17-44 (1983).
Smets, G. et al., "Photomechanical effects in photochromic systems," Pure Appl Chem, 50:845-56 (1978).
Stachera, D. et al., "Acid recovery using diffusion dialysis with poly(4-vinylpyridine)-filled microporous membranes," J Membrane Sci, 148:119-27 (1998).
Supplementary European Seach Report dated Apr. 26, 2007 (dated May 8, 2007) from EP 05 732 196.0.
Supplementary European Seach Report dated Apr. 7, 2009 (dated May 8, 2009) from EP 05 75 3128.7.
Supplementary European Search Report dated Aug. 20, 2013, from EP 09 81 2101.
Supplementary European Search Report dated Jul. 4, 2014, from EP 10 82 9596.
Supplementary European Search Report dated Oct. 8, 2014, from EP 12786567.3.
Svec et al., "Molded Rigid Monolithic Porour Polymers: An Inexpensive, Efficient, and Versatile Alternative to Beads for the Design of Materials for Numerous Applications," Ind. Eng. Chem. Res., 38:34-48 (1999).
Svec, F. et al., "Reactive macroporous membranes based on glycidyl methacrylate-ethylene dimethacrylate copolymer for high-performance membrane chromatography of proteins," Angew Makromol Chem, 188:167-76 (1991).

(56) References Cited

OTHER PUBLICATIONS

Svec, F., et al., "Kinetic Control of Pore Formation in Macroporous Polymers. Formation of "Molded" Porous Materials with High Flow Characteristics for Separation or Catalysis", Chem. Mater. (1995) vol. 7, p. 707-715.

Tennikov, M.B. et al., "Effect of porous structure of macroporous polymer supports on resolution in high-performance membrane chromatography of proteins," J Chromatogr A, 798:55-64 (1998).

Tennikova et al., "High-performance membrane chromatography of proteins, a novel method of protein separation," Chromatogr, 555:97-107 (1991).

Tennikova et al., "High-performance membrane chromatography. A novel method of protein separation," J Liq Chromatogr, 13: 63-70 (1990).

Tennikova et al., "High-performance membrane chromatography: highly efficient separation method for proteins in ion-exchange, hydrophobic interaction and reversed-phase modes," J Chromatogr, 646: 279-288 (1993).

Ultrafiltration, Nanofiltration and Reverse Osmosis, SDWF, <<www.safewater.org>>; on Apr. 20, 2010, during prosecution of U.S. Appl. No. 11/547,736; no date provided.

Van Krevelen, D.W., "Cohesive Properties and Solubility," Properties of Polymers, 2nd Ed., Elsevier, Amsterdam, Chapter 7, p. 129-159 (1976).

Vijayalakshmi, M.A., "Antibody Purification Methods," Applied Biochemistry and Biotechnology, 75:93-102 (1998).

Viklund et al., "Fast ion-exchange HPLC of proteins using porous poly(glycidyl methacrylate-co-ethylene dimethacrylate) monoliths grafted with poly(2-acrylamido-2-methyl-1-propanesulfonic acid)," Biotechnol Progr, 13:597-600 (1997).

Von Gottberg, A., "New high-performance spacers in electrodialysis reversal (EDR) systems," Proceedings—Annual Conference, American Water Works Association (1998) p. 215-229, vol. B, Water Resources.

Wang et al., "Polymeric Porogens Used in he Preparation of Novel Monodispersed Macroporous Polymeric Separation Media for High-Performance Liquid Chromatography," Anal. Chem., 64:1232-1238 (1992).

Wang, L., "Internal surface coating and photochemical modification of polypropylene microfiltration membrane", Ph.D. Thesis, McMaster University, Hamilton, Ont., Canada, (1997).

Warwick, T. et al., "A scanning transmission x-ray microscope for materials science spectromicroscopy at the advanced light source," Rev Sci Instrum, 69(8):2964-73 (1998).

Warwick, T. et al., "Soft x-ray spectromicroscopy development for materials science at the advanced light source," J Electron Spectrosc, 84:85-98 (1997).

Webber, R.M. et al., "Hydrodynamic studies of adsorbed diblock copolymers in porous membranes," Macromolecules, 23:1026-34 (1990).

Xie et al., "Rigid porous polyacrylamide-based monolithic cols. containing butyl methacrylate as a separation medium for the rapid hydrophobic interaction chromatography of proteins," Journal of Chromatography, 775:65-72 (1997).

Yang et al., "Hollow fiber membrane chromatography: A novel analytical system for trace metal separation," Analytica Chimia Acta, 369:17-20 (1998).

Yang, H., "Analysis of protein purification using ion-exchange membranes," Ind Eng Chem, 38:4044-50 (1999).

Yonese, M. et al., "Visoelastic properties of poly (vinyl alcohol)/alginate snake-cage hydrogels and interpenetrating hydrogels," Polym J, Society of Polymer Science, Tokyo, JP, 24(4):395-404 (1992).

Youtube video titled "Membrane Chromatography for MAB Purification—Natrix Separations 2010," uploaded Jan. 18, 2011 and retrieved from the Internet on Aug. 15, 2014 (URL:https://www.youtube.com/watch?v=uKTEby4n21g).

Zhang, H.Q. et al., "Synthesis and characterization of novel photochromic side-chain liquid crystalline polymethacrylates containing para-nitroazobenzene group," Eur Polym J, 34(10):1521-9 (1998).

\* cited by examiner

CHROMATOGRAPHY MEMBRANES, DEVICES CONTAINING THEM, AND METHODS OF USE THEREOF

RELATED APPLICATIONS

This application is a continuation of U.S. application Ser. No. 16/100,515, filed Aug. 10, 2018; which is a continuation of U.S. application Ser. No. 15/427,447, filed on Feb. 8, 2017; which is a continuation of U.S. application Ser. No. 12/551,762, filed Sep. 1, 2009; which claims the benefit of priority to U.S. Provisional Patent Application Ser. No. 61/093,600, filed on Sep. 2, 2008; and U.S. Provisional Application Ser. No. 61/102,797, filed on Oct. 3, 2008.

BACKGROUND OF THE INVENTION

Membrane-based water treatment processes were first introduced in the 1970s. Since then, membrane-based separation technologies have been utilized in a number of other industries. In the pharmaceutical and biotechnology industries, the use of preparative chromatography, direct flow filtration (DFF) and tangential flow filtration (TFF), including micro-, ultra-, nano-filtration and diafiltration are well-established methods for the separation of dissolved molecules or suspended particulates. Ultrafiltration (UF) and microfiltration (MF) membranes have become essential to separation and purification in the manufacture of biomolecules. Biomolecular manufacturing, regardless of its scale, generally employs one or more steps using filtration. The attractiveness of these membrane separations rests on several features including, for example, high separation power, and simplicity, requiring only the application of pressure differentials between the feed stream and the permeate. This simple and reliable one-stage filtering of the sample into two fractions makes membrane separation a valuable approach to separation and purification.

Notably, the separation and recovery of biomolecules, such as enzymes and glycoproteins, are critical cost-determining steps in most of the down-stream processes in the biotechnology industry. For example, separation of lysozyme from crude sources, such as egg white, has been achieved by salt precipitation (U.S. Pat. No. 4,504,583), or ion exchange techniques (U.S. Pat. Nos. 4,705,755; 4,966,851; 4,518,695; and 4,104,125). Due to the viscous, highly concentrated nature of egg white, and the nature of the other protein constituents, recovering high-purity lysozyme in good yield is extremely laborious and costly.

In one class of membrane separations, the species of interest is that which is retained by the membrane, in which case the objective of the separation is typically to remove smaller contaminants, to concentrate the solution, or to affect a buffer exchange using diafiltration. In another class of membrane separations, the species of interest is that which permeates through the filter, and the objective is typically to remove larger contaminants. In MF, the retained species are generally particulates, organelles, bacteria or other microorganisms, while those that permeate are proteins, colloids, peptides, small molecules and ions. In UF the retained species are typically proteins and, in general, macromolecules, while those that permeate are peptides, ions and, in general, small molecules.

In "dead-end," "normal flow," or "direct flow" filtration (DFF), a filtration device is used that has one inlet and one outlet. The total (100%) solution volume is forced through a porous filter. DFF devices are commonly single-use devices. Such membrane filters or depth filters are commercially available in different filter area sizes as well as different pore sizes. Depending upon the selected pore size, molecules or particulates smaller than the average membrane pore size will pass (together with solvent) through the filter. Thus, direct flow filtration (DFF) devices allow for the selective removal of particulates, bacteria, viruses, cell debris, and large macromolecules.

Conventional filters in which all of the fluid entering the filter housing passes through the filter element (DFF) typically operate at low shear near the surface of the filter medium. Thus, when a highly flocculating dispersion is delivered into a conventional filter device by a conventional delivery system, flocs ordinarily tend to form near the surface of the filter medium. The flow field moves the flocs onto the surface and into the bulk of the filter medium, ultimately resulting in plugging of the filter. In practice, a plugged filter may cause a significant amount of downtime for a filter change.

A raw or semi-conditioned process stream that contains high-value materials is often highly viscous or highly contaminated. As such, DFF separation approaches are difficult or challenging due to blinding of the membrane with the solute present in the feed stream. Additionally, these processes often require high pressure to maintain a reasonable flux of permeate.

In contrast, tangential flow filtration (TFF) devices, also known as cross-flow filtration devices, have one inlet, one retentate outlet and at least one permeate outlet. Tangential flow denotes a filtration configuration in which a flowing fluid is directed along the surface of a filter medium, substantially parallel (tangential) to the surface of the filter medium. In this configuration, the solute adsorbs or absorbs to the surface or the pores of the membrane as the eluent flows over the surface. The purified portion of fluid that passes through such filter medium has a velocity component which is "cross-wise", i.e., perpendicular to the direction of the fluid flowing along the surface of such filter medium. In TFF, the retentate (or decantate) can be repeatedly re-circulated with the objective of improving filtration efficiency and enhancing the permeate yield. The re-circulated retentate solution pathway runs parallel to the membrane surface and is pumped past the membrane with sufficient velocity to ensure a surface cleaning action. However, only a relatively small amount of permeate is collected during each retentate volume-pass, and thus a significant processing time is typically associated with TFF procedures. If an appropriate membrane is selected for a specific separation, a second liquid can be used to elute the material adsorbed or absorbed to the membrane for harvesting.

Crossflow filtration or tangential filtration is a well known filtration process. Reference may be had e.g., to U.S. Pat. Nos. 5,681,464, 6,461,513; 6,331,253, 6,475,071, 5,783,085, 4,790,942, the disclosures of which are incorporated herein by reference. Reference may also be had to "Filter and Filtration Handbook", 4th Ed., T. Christopher Dickenson, Elsevier Advanced Technology, 1997, the disclosure of which is incorporated herein by reference.

In TFF careful attention must be paid in the device design, as flow dynamics play an important role in the efficiency of the system. Turbulent flow must be minimized in these systems, so as to not physically disassociate a desired substance from the membrane surface. Turbulence is flow dominated by recirculation, eddies, and apparent randomness. Flow in which turbulence is not exhibited is called laminar. A steady, laminar flow is desired.

For optimal results, both DFF and TFF demand careful attention to filter porosity and filter area, as well as required differential pressures and selected pump rates. However, filtration devices tend to clog when used over an extended period of time and must be timely replaced. Clogging of a filtration device occurs: (1) when the membrane pores become obstructed, typically with trapped cells, particulate matter, cell debris or the like, or (2) when the feed channel (into a TFF device) becomes obstructed by solids or colloidal material and/or cell debris. This clogging of the feed channel or membrane pores results in a decreased liquid flow across the porous filter membrane. The result is a change in system pressure which, if not properly addressed, runs the risk of serious detriment to the operation which incorporates the filtration procedure.

As such, the choice of membrane in each of the filtration techniques is critical to the efficiency and success of the separation. Composite membranes with high specificity and high binding capacity have been described in U.S. Pat. No. 7,316,919, and US Patent Application Publication Nos. 2008/0314831 and 2008/0312416, which are hereby incorporated by reference in their entirety. These materials are highly versatile and can be designed for specific separation situations.

A wide variety of devices are available for these applications. Typically, devices are categorized by configuration into categories including the following: flat plate (for example, cassette or plate and frame), spiral (or spiral wound), tubular, or hollow fiber. The choice of device configuration is driven by reliability, performance, and cost for each specific application.

Flat plate or cassette devices consist of membranes cast on plates; the plates are then reliably stacked. The devices may or may not have flexible screens in the feed channels to support the membranes. An appealing advantage of a configuration such as this is its very compact design. However, channel height control, defined by plate-to-plate interaction and distance, must be very carefully considered Tubular devices consist of a membrane cast on the inside surface or outside diameter of a porous support tube. Typically, a feed solution is pumped through the center of the tube at velocities as high as 20 ft/s. These cross-flow velocities minimize the formation of a concentration polarization layer on the membrane surface, promoting high and stable flux and easy cleaning. The permeate is driven through the membrane. Despite the apparent advantages of using a system such as this, the cost tends to be high.

Spiral-wound devices consist of multiple layers of folded membrane, feed screen, and permeate screen wound around a center permeate collection tube (FIG. 23). Typically found in water purification applications, these devices are also compact and can operate at low pressure to save energy, but are suitable for high pressure applications as well. The cost per membrane area is typically low.

Typical spiral wound filters consist of about 1 to about 6 spiral wound elements coupled in a serial flow mode and placed in a cylindrical pressure vessel. Between two membranes in the roll is placed a permeable porous medium for conduction of fluid, the concentrate spacer, to ensure that the concentrate can flow over the membrane in order to be distributed all over the surface and to continuously rinse the membrane from accumulating solids. The filter elements are kept tightly wound by a hard, impermeable shell. In this configuration flow in and out of the filter element will be through the ends in an axial direction.

An unmet need exists in many applications where high contaminate feed streams will immediately plug or blind the membrane media in a typical DFF mode or, when the membranes employed are incapable of any appreciable substrate capture, in cross-flow modes. Utilizing versatile, high performance, high throughput membranes capable of high binding capacities in filtration devices would provide separation systems with performances far exceeding any known technology in a variety of art areas.

SUMMARY OF THE INVENTION

In certain embodiments, the invention relates to a fluid treatment device comprising a housing unit, wherein the housing unit comprises
  (a) an inlet and an outlet;
  (b) a fluid flow path between the inlet and the outlet; and
  (c) a composite material within the housing unit, wherein the composite material comprises
    a support member comprising a plurality of pores extending through the support member; and
    a non-self-supporting macroporous cross-linked gel comprising macropores having an average size of 10 nm to 3000 nm, said macroporous gel being located in the pores of the support member;
    wherein said macropores of said macroporous cross-linked gel are smaller than said pores of said support member;
wherein the pores of the support member are substantially perpendicular to the fluid flow path.

In certain embodiments, the invention relates to a fluid treatment device comprising
  a plurality of housing units, wherein each housing unit comprises
  (a) an inlet and an outlet;
  (b) a fluid flow path between the inlet and the outlet; and
  (c) a composite material within the housing unit, wherein the composite material comprises
    a support member comprising a plurality of pores extending through the support member; and
    a non-self-supporting macroporous cross-linked gel comprising macropores having an average size of 10 nm to 3000 nm, said macroporous gel being located in the pores of the support member;
    wherein said macropores of said macroporous cross-linked gel are smaller than said pores of said support member; and
wherein the pores of the support member are substantially perpendicular to the fluid flow path.

In certain embodiments, the invention relates to any one of the aforementioned fluid treatment devices, wherein the composite material is arranged in a substantially coplanar stack of substantially coextensive sheets, a substantially tubular configuration, or a substantially spiral wound configuration.

In certain embodiments, the invention relates to any one of the aforementioned fluid treatment devices, wherein the macroporous cross-linked gel is a neutral or charged hydrogel, a polyelectrolyte gel, a hydrophobic gel, a neutral gel, or a gel comprising functional groups.

In certain embodiments, the invention relates to any one of the aforementioned fluid treatment devices, wherein said functional groups are selected from the group consisting of amino acid ligands, antigen and antibody ligands, dye ligands, biological molecules, biological ions, and metal affinity ligands.

In certain embodiments, the invention relates to any one of the aforementioned fluid treatment devices, wherein said functional groups are metal affinity ligands. In certain embodiments, the invention relates to any one of the aforementioned fluid treatment devices, further comprising a plurality of metal ions complexed to a plurality of said metal affinity ligands. In certain embodiments, the invention relates to any one of the aforementioned fluid treatment devices, wherein said metal affinity ligands are iminodicarboxylic acid ligands; and said metal ions are nickel.

In certain embodiments, the invention relates to any one of the aforementioned fluid treatment devices, wherein said functional groups are biological molecules or biological ions. In certain embodiments, the invention relates to any one of the aforementioned fluid treatment devices, wherein said functional groups are Protein A.

In certain embodiments, the invention relates to a method comprising the step of:

contacting a first fluid comprising a substance with a composite material in any one of the aforementioned fluid treatment devices, thereby adsorbing or absorbing the substance onto the composite material.

In certain embodiments, the invention relates to any one of the aforementioned methods, further comprising the step of placing the first fluid in an inlet of the fluid treatment device.

In certain embodiments, the invention relates to any one of the aforementioned methods, wherein the first fluid is passed along a fluid flow path substantially perpendicular to the pores of the support member.

In certain embodiments, the invention relates to any one of the aforementioned methods, further comprising the step of contacting a second fluid with the substance adsorbed or absorbed onto the composite material, thereby releasing the substance from the composite material.

In certain embodiments, the invention relates to any one of the aforementioned methods, wherein the first fluid is a suspension of cells or a suspension of aggregates.

In certain embodiments, the invention relates to any one of the aforementioned methods, wherein the substance is a biological molecule or biological ion. In certain embodiments, the invention relates to any one of the aforementioned methods, wherein the biological molecule or biological ion is a protein; and the protein comprises exposed His amino acid residues. In certain embodiments, the invention relates to any one of the aforementioned methods, wherein the biological molecule or biological ion is a monoclonal antibody.

In certain embodiments, the invention relates to any one of the aforementioned methods, wherein the substance is a metal-containing particle, or a metal-containing ion.

In certain embodiments, the invention relates to any one of the aforementioned methods, wherein the first fluid is waste water.

In certain embodiments, the invention relates to any one of the aforementioned methods, wherein the first fluid comprises egg white; and the substance is lysozyme.

DETAILED DESCRIPTION OF THE INVENTION

Overview

Figure 1:
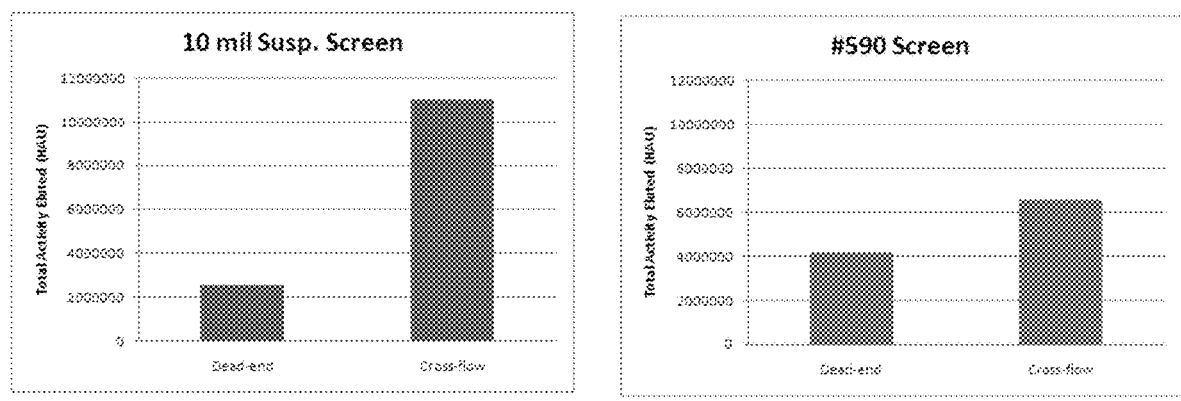
FIG. 1 depicts the results of dead-end compared to cross-flow modes for viral capture using an ion-exchange membrane. In both cases, the lower value obtained with dead-end flow was due to fouling of the membrane during the experiment.

Disclosed is a hydrophilic, high binding, high throughput chromatography membrane that is effective for selective capture of target materials, such as bio-molecules, from raw or dirty process streams. This capture process can be accomplished by binding of the target molecules at the surface or near surface of the membrane media ("cross-flow" mode), as opposed to the more typical trans-membrane mode. The captured target species can be collected in a highly purified form in subsequent procedures. These final steps are chromatographic in nature and allow for controlled separation of the target materials. Importantly, the collection step and the separation step can be done in either tangential flow or in trans-membrane flow or combinations thereof. See, e.g., FIG. 1.

Exemplary device designs suitable for this process include those in which the membrane is incorporated into a modified cassette, wrap, or spiral-wound cross-flow separation device designed for low-shear fluid-flow, and minimization of uncontrolled or undesired trans-membrane flow. For example, such devices were found to be effective for separating proteins or viruses from highly viscous and or highly contaminated feed streams with a minimum of process fluid flux across the membrane. The cross flow (tangential flow) format allows for greater flexibility in washing and eluting the target molecule(s). The cross flow devices can be run in feed-to-retentate mode and perform a surface ion exchange or affinity separation. Washing can be done in feed-to-retentate mode, feed-to-permeate or permeate-to-feed mode, or in a sequential mode.

The incorporation of the hydrophilic, high performance chromatography membrane into a modified cross flow device provides a separation device that purifies target molecules from highly viscous or high particulate feed streams, and completes both clarification and capture of target species with no intervening steps. Moreover, the materials and constructs described here do not preclude the use of the same membrane materials in traditional device designs, such as pleated dead-end capsules. Importantly, these products can produce highly purified proteins, vaccines, or nutraceuticals from feed streams that cannot be processed directly with current commercial technology. Additionally, the devices and methods of the present invention allow for faster processing of large volumes of feed streams than any current technology.

For example, due to the viscous, highly concentrated nature of egg white, typical filtration schemes prove to be problematic when trying to collect constituents present in relatively low concentrations. Using the devices and methods of the present invention, lysozyme can be easily separated from egg white with high recovery and high purity.

In certain embodiments, the invention relates to a device that displays superior performance in comparison to know devices. In certain embodiments, the devices may tolerate about 10× to about 100× higher throughput than resins. In certain embodiments, the devices may display up to about 25× higher binding capacity than existing chromatographic membranes and resins.

In certain embodiments, the invention relates to a device that is scalable and produces predictable results in the transitions from Lab to Pilot to Production, unlike conventional resin products.

In certain embodiments, the invention relates to a device that encompasses a robust technology. In certain embodiments, the superior mechanical strength of the devices and the inherent hydrophilicity of the composite membranes lead to longer in-process product lifetimes and more consistent performance.

In certain embodiments, the invention relates to a device that may be available as a single use or multi-cycle disposable unit. This flexibility may eliminate costly and time consuming cleaning and storage validation. Furthermore, the devices of the invention enable simple process and may improve regulatory compliance.

In certain embodiments, the invention relates to separation processes that may require reduced buffer usage. In certain embodiments, using devices of the present invention may eliminate the need for column cleaning, equilibration, or storage in expensive buffers. In certain embodiments, the devices of the invention may tolerate higher concentration feed stream, so no dilution may be needed.

In certain embodiments, using the devices described herein may lower capital expenses and may offer significant operational cost savings for a client. In certain embodiments, the devices of the invention may have a lower initial cost and faster delivery. In certain embodiments, the devices allow for lower staffing requirements and reduced maintenance costs.

In certain embodiments, the invention relates to a device with a small footprint. In certain embodiments, the devices of the invention exhibit higher binding capacity and require less floor space than typical resin bed chromatography devices.

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

In describing the present invention, a variety of terms are used in the description. Standard terminology is widely used in filtration, fluid delivery, and general fluid processing art.

The articles "a" and "an" are used herein to refer to one or to more than one (i.e., to at least one) of the grammatical object of the article. By way of example, "an element" means one element or more than one element.

The term "associated with" as used herein in such phrases as, for example, "an inorganic metal oxide associated with an stabilizing compound," refers to the presence of either weak or strong or both interactions between molecules. For example weak interactions may include, for example, electrostatic, van der Waals, or hydrogen-bonding interactions. Stronger interactions, also referred to as being chemically bonded, refer to, for example, covalent, ionic, or coordinative bonds between two molecules. The term "associated with" also refers to a compound that may be physically intertwined within the foldings of another molecule, even when none of the above types of bonds are present. For example, an inorganic compound may be considered as being in association with a polymer by virtue of it existing within the interstices of the polymer.

The terms "comprise" and "comprising" are used in the inclusive, open sense, meaning that additional elements may be included.

The term "including" is used to mean "including but not limited to." "Including" and "including but not limited to" are used interchangeably.

The term "polymer" is used to mean a large molecule formed by the union of repeating units (monomers). The term polymer also encompasses copolymers.

The term "co-polymer" is used to mean a polymer of at least two or more different monomers. A co-polymer can be comprised of a cross-linker and a monomer, if the cross-linker is a difunctional monomer.

The term "two phase fluid" is used to mean a fluid comprising a liquid phase in which either substantially solid particles are dispersed therethrough, or a first liquid phase in which droplets or particles of a second liquid phase immiscible with such first liquid phase are dispersed through such first liquid phase. A "multiphase fluid" is used to mean a fluid comprising a first liquid phase in which at least one additional second solid or liquid phase is dispersed therethrough.

The term "particle" is used to mean a discreet liquid droplet or a solid object, with a characteristic dimension such as a diameter or length of between about one nanometer, and about one-tenth of a meter.

The term "particle size" is used to mean a number-average or weight-average particle size as measured by conventional particle size measuring techniques well known to those skilled in the art, such as dynamic or static light-scattering, sedimentation field-flow fractionation, photon-correlation spectroscopy, or disk centrifugation. By "an effective average particle size of less than about 1000 nm" it is meant that at least about 90% of the particles have a number-average or weight-average particle size of less than about 1000 nm when measured by at least one of the above-noted techniques. The particular size of particles in a fluid being processed will depend upon the particular application.

The term "interstices" is used to mean a space, especially a small or narrow one, between things or parts.

The term "dispersion" is used to mean any fluid comprising a liquid phase in which substantially solid particles are suspended, and remain suspended, at least temporarily.

The term "slurry" is used to mean any fluid comprising a liquid phase in which substantially solid particles are present. Such particles may or may not be suspended in such fluid.

The term "emulsion" is used to mean any fluid comprising a first liquid phase within which droplets or particles of a substantially liquid second phase are suspended, and remain suspended, at least temporarily. In reference to discreet entities of a second liquid phase in a first liquid phase, the terms "droplets" and "particles" are used interchangeably herein.

The term "crossflow" in reference to filtration is used to mean a filtration configuration in which a flowing fluid is directed along the surface of a filter medium, and the portion of fluid that passes through such filter medium has a velocity component which is "cross-wise", i.e., perpendicular to the direction of the fluid flowing along the surface of such filter medium.

The term "tangential filtration" is used to mean a filtration process in which a flowing fluid is directed substantially parallel (i.e., tangential) to the surface of a filter medium, and a portion of fluid passes through such filter medium to provide a permeate. The terms "tangential filtration" and "crossflow filtration" are often used interchangeably in the art.

The term "permeate" is used to mean the portion of the fluid that passes through the filter medium and out through a first outlet port in the filter device that is operatively connected to such filter medium. The term "decantate" is used to mean the portion of the fluid that flows along the surface of the filter medium, but does not pass through such filter medium, and passes out through a second outlet port in the filter device that is operatively connected to such filter medium.

Crossflow filtration and tangential filtration are well known filtration processes. Reference may be had to, e.g., U.S. Pat. Nos. 5,681,464, 6,461,513; 6,331,253, 6,475,071, 5,783,085, 4,790,942, the disclosures of which are incorporated herein by reference. Reference may also be had to "Filter and Filtration Handbook", 4th Ed., T. Christopher Dickenson, Elsevier Advanced Technology, 1997, the disclosure of which is incorporated herein by reference.

The term "egg white" refers to the clear, aqueous liquid contained within an egg, as opposed to the yellow egg yolk. Egg white typically comprises about 15% proteins dissolved or suspended in water. Egg white proteins typically include ovalbumin, ovotransferrin, ovomucoid, globulins, lysozyme, ovomucin, and avidin.

Exemplary Devices

General Device Properties

In certain embodiment, the invention relates to a fluid treatment device comprising a housing unit, wherein the housing unit comprises
  (a) an inlet and an outlet;
  (b) a fluid flow path between the inlet and the outlet; and
  (c) a composite material within the housing unit, wherein the composite material comprises
     a support member comprising a plurality of pores extending through the support member; and
     a non-self-supporting macroporous cross-linked gel comprising macropores having an average size of 10 nm to 3000 nm, said macroporous gel being located in the pores of the support member;
  wherein said macropores of said macroporous cross-linked gel are smaller than said pores of said support member; and wherein the pores of the support member are substantially perpendicular to the fluid flow path.

In certain embodiments, the invention relates to any one of the above-mentioned fluid treatment devices, wherein the composite material is arranged in a substantially coplanar stack of substantially coextensive sheets, a substantially tubular configuration, or a substantially spiral wound configuration.

In certain embodiments, the invention relates to any one of the above-mentioned fluid treatment devices, wherein the composite material has 2 to 10 separate support members.

In certain embodiments, the invention relates to any one of the above-mentioned fluid treatment devices, wherein
the support member is in the form of hollow porous fibers;
each hollow porous fiber defines a lumen;
the lumen is from about 20 µm to about 100 µm in diameter; and
the lumen is substantially perpendicular to the pores in the hollow porous fiber support member.

In certain embodiments, the invention relates to any one of the above-mentioned fluid treatment devices, wherein a plurality of hollow porous fibers are arranged in a bundle.

In certain embodiments, the invention relates to any one of the above-mentioned fluid treatment devices, wherein the bundle is encased in a shell or a vessel.

In certain embodiments, the invention relates to any one of the above-mentioned fluid treatment devices, wherein a plurality of bundles is encased in a shell or a vessel.

In certain embodiments, the invention relates to any one of the above-mentioned fluid treatment devices, wherein the hollow porous fiber comprises a cap, a plug, or a seal. In certain embodiments, the invention relates to any one of the above-mentioned fluid treatment devices, wherein the hollow porous fiber comprises a cap, a plug, or a seal on both ends. In certain embodiments, the end of the hollow porous fiber is "potted" such that the inside of the fiber is isolated from the outside of the fiber. In certain embodiments, this is accomplished through the use of a tubesheet. In certain embodiments, the potting material to form the tubesheet may be comprised of any suitable material. In certain embodiments, the potting material can be in liquid form when preparing the tubesheet and can thereafter be solidified, e.g., by cooling, curing, or the like. In certain embodiments, the solidified potting material should exhibit sufficient structural strength for providing a tubesheet and be relatively inert moieties to which it will be exposed during fluid separation operation. In certain embodiments, the potting material may be organic material (for example, epoxy), inorganic material, or organic material containing inorganic material, and the potting material may be natural or synthetic. In certain embodiments, typical inorganic materials include glasses, ceramics, cermets, metals and the like.

In certain embodiments, the hollow porous fiber may be of any convenient configuration. In certain embodiments, the hollow porous fiber is circular, hexagonal, trilobal, or the like in cross-section and may have ridges, grooves, or the like extending inwardly or outwardly from the walls of the hollow porous fibers. In certain embodiments, the hollow porous fiber may have an inner diameter of about 20 microns to about 200 microns. In certain embodiments, the hollow porous fiber may have an inner diameter of about 40 microns. In certain embodiments, the hollow porous fiber may have a hollow ratio (being the area of the fiber bore divided by the area of the total cross-section of the fiber) of about 10% to about 50% percent. In certain embodiments, the hollow porous fiber may have a hollow ratio of about 20%. In certain embodiments, the hollow porous fiber may be fabricated from various polymers such as cellulose, cellulose esters, cellulose ethers, polyamides, silicone resins, polyurethane resins, unsaturated polyester resins or the like, or ceramics.

In certain embodiments, the invention relates to any one of the above-mentioned fluid treatment devices, wherein the composite material is a pleated membrane.

In certain embodiments, the invention relates to any one of the above-mentioned fluid treatment devices, wherein the housing unit is substantially cylindrical. In certain embodiments, the housing unit has an inner diameter of from about 5 cm to about 50 cm.

In certain embodiments, the thickness of the walls of the housing unit may be adapted to the specific operation conditions.

In certain embodiments, the invention relates to any one of the above-mentioned fluid treatment devices, wherein the housing unit is disposable or reusable.

In certain embodiments, the invention relates to any one of the above-mentioned fluid treatment devices, wherein the housing unit is plastic or stainless steel.

In certain embodiments, the invention relates to a fluid treatment device comprising a housing unit, wherein the housing unit comprises
at least one inlet and at least one outlet; and
a fluid flow path between the inlet and the outlet; wherein any one of the above-mentioned fluid treatment elements is across the fluid flow path.

In certain embodiments, the invention relates to any one of the above-mentioned fluid treatment devices, wherein the composite material comprises:
(a) a support member comprising a plurality of pores extending through the support member; and
(b) a non-self-supporting macroporous cross-linked gel comprising macropores having an average size of 10 nm to 3000 nm, said macroporous gel being located in the pores of the support member;
wherein
said macroporous cross-linked gel is present in the pores of the support member in an amount sufficient such that, in use, liquid passing through the composite material passes through said macropores of said macroporous cross-linked gel;
said macropores of said macroporous cross-linked gel are smaller than said pores of said support member;
the support member is in the form of hollow porous fibers; each hollow porous fiber defines a lumen;
the lumen is from about 20 µm to about 100 µm in diameter; and
the lumen is substantially perpendicular to the pores in the hollow porous fiber support member.

In certain embodiments, the fluid treatment devices comprise the above-mentioned composite material, wherein a plurality of hollow porous fibers is arranged in a bundle. In certain embodiments, the fluid treatment devices comprise the above-mentioned composite material, wherein the bundle is encased in a shell. In certain embodiments, the fluid treatment devices comprise the above-mentioned composite material, wherein the bundle is encased in a vessel. In certain embodiments, the fluid treatment devices comprise the above-mentioned composite material, wherein a plurality of bundles is encased in a shell. In certain embodiments, the fluid treatment devices comprise the above-mentioned composite material, wherein a plurality of bundles is encased in a vessel.

In certain embodiments, the invention relates to a fluid treatment device comprising a plurality of housing units, wherein each housing unit comprises
(a) an inlet and an outlet;
(b) a fluid flow path between the inlet and the outlet; and
(c) a composite material within the housing unit, wherein the composite material comprises
a support member comprising a plurality of pores extending through the support member; and
a non-self-supporting macroporous cross-linked gel comprising macropores having an average size of 10 nm to 3000 nm, said macroporous gel being located in the pores of the support member;
wherein said macropores of said macroporous cross-linked gel are smaller than said pores of said support member; and
wherein the pores of the support member are substantially perpendicular to the fluid flow path.

In certain embodiments, the invention relates to any one of the above-mentioned fluid treatment devices, wherein the plurality of housing units are arranged in series.

In certain embodiments, the invention relates to any one of the above-mentioned fluid treatment devices, comprising from about 2 to about 10 housing units.

In certain embodiments, the invention relates to any one of the above-mentioned fluid treatment devices, wherein the composite material is arranged in a substantially coextensive stack of substantially coplanar sheets; a substantially tubular configuration; or a substantially spiral wound configuration.

In certain embodiments, wherein the inlet or the outlet is a press fit attachment point, a luer lock attachment point, or a hose barb attachment point. In certain embodiments, the inlet is a press fit, luer lock, or hose barb attachment points. In certain embodiments, the outlet is a press fit, luer lock, or hose barb attachment points. In certain embodiments, the inlet and the outlet are different kinds of attachment points from one another. In certain embodiments, the inlet and the outlet are both press fit attachment points. In certain embodiments, the inlet and the outlet are both luer lock attachment points. In certain embodiments, the inlet and the outlet are both hose barb attachment points.

Laboratory-Scale

In certain embodiments, the invention relates to any one of the above-mentioned fluid treatment devices, wherein the composite material is a cut disk membrane. In certain embodiments, the cut disks are intended to be used in re-usable housings. In certain embodiments, the cut disks are intended to be used in disposable housings. In certain embodiments, the cut disk membrane is substantially circular in shape.

In certain embodiments, the invention relates to any one of the above-mentioned fluid treatment devices, wherein the composite material is a cut disk membrane. In certain embodiments, the cut disk membrane is from about 15 to about 60 mm in diameter. In certain embodiments, the cut disk membrane is from about 20 to about 55 mm in diameter. In certain embodiments, the cut disk membrane is about 25 mm in diameter. In certain embodiments, the cut disk membrane is about 50 mm in diameter. For visualization of certain embodiments, see FIGS. 9-17.

In certain embodiments, the invention relates to any one of the above-mentioned fluid treatment devices, wherein the housing unit is a syringe tip. The term "syringe column" is used interchangeably with the term "syringe tip."

In certain embodiments, the invention relates to any one of the above-mentioned fluid treatment devices, wherein the housing unit is a syringe column; and the composite material is in the form of a cut disk. In certain embodiments, the syringe column housing unit is semi-disposable.

In certain embodiments, the invention relates to any one of the above-mentioned fluid treatment devices, wherein the housing unit is a spin column. In certain embodiments, the invention relates to any one of the above-mentioned fluid treatment devices, wherein the housing unit is a spin column; and the composite material is in the form of a cut disk. A spin column is a tube with an upper and a lower half. The lower half is closed at the bottom. In between the two halves is a cut disk membrane held or suspended in some manner. A user loads the top half with a liquid containing the target (or contaminate) solute and places the spin column into a centrifuge. The centrifuge forces the liquid through the membrane when run at sufficient RPM. Once removed from the centrifuge, the lower half of the device can be removed and the liquid collected (if needed) or the top half can be eluted with additional buffer to remove the retained solute. In certain embodiments, the spin columns can be made in many sizes.

In certain embodiments, the invention relates to any one of the above-mentioned fluid treatment devices, wherein the housing unit is a spin column; and the spin column has a capacity of from about 0.1 mL to about 60 mL. In certain embodiments, the volume of the spin column refer to the quantity of feed stream that may be processed by an exemplary fluid treatment device. In certain embodiments, the spin column has a capacity of from about 0.3 mL to about 55 mL. In certain embodiments, the spin column has a capacity of about 0.5 mL. In certain embodiments, the spin column has a capacity of about 2 mL. In certain embodiments, the spin column has a capacity of up to about 50 mL. For visualization of certain embodiments, see, e.g., FIGS. 18-22.

Process- and Manufacturing-Scale

In certain embodiments, the invention relates to any one of the above-mentioned fluid treatment devices, wherein the housing unit is a cassette configuration.

In certain embodiments, the invention relates to any one of the above-mentioned fluid treatment devices, wherein the housing unit is a tubular configuration.

In certain embodiments, the invention relates to any one of the above-mentioned fluid treatment devices, wherein the housing unit is a spiral wound configuration.

In certain embodiments, the invention relates to any one of the above-mentioned fluid treatment devices, wherein the housing unit is a plate and frame configuration.

In certain embodiments, the invention relates to any one of the above-mentioned fluid treatment devices, wherein the housing unit comprises a fluid treatment element, wherein the fluid treatment element comprises a hollow porous membrane.

Exemplary Fluid Treatment Elements

In certain embodiments, the invention relates to fluid treatment elements. In certain embodiments, the fluid treatment element is a cartridge for use in a fluid treatment device of the present invention. In certain embodiments, the invention relates to fluid treatment elements comprising membranes. In certain embodiments, the invention relates to fluid treatment elements comprising composite materials for use as membranes.

In certain embodiments, the fluid treatment elements are disposable or reusable.

In certain embodiments, the invention relates to any one of the above-mentioned fluid treatment elements, wherein the element comprises a hollow, generally cylindrical form.

In certain embodiments, the fluid treatment elements of the present invention accommodate high solid density materials. In certain embodiments, the fluid treatment elements of the present invention are used for their strength. In certain embodiments, the fluid treatment elements of the present invention are used in heavy duty applications. In certain embodiments, the fluid treatment elements of the present invention can tolerate elevated temperatures for sustained periods.

In certain embodiments, the fluid treatment elements of the present invention exhibit reduced capture time in chromatography applications. In certain embodiments, the fluid treatment elements of the present invention exhibit high binding capacities.

Exemplary Composite Materials

In certain embodiments, the invention relates to any one of the above-mentioned fluid treatment devices or elements comprising a composite material. In certain embodiments, the invention comprises a composite material for use as a membrane.

In certain embodiments, the composite materials used as membranes in the present invention are described in U.S. Pat. No. 7,316,919; and U.S. patent application Ser. Nos. 11/950,562, 12/108,178, 12/244,940, 12/250,861, 12/211,618, and 12/250,869; all of which are hereby incorporated by reference.

In certain embodiments, the invention relates to any one of the above-mentioned fluid treatment devices or elements, wherein the macroporous crosslinked gel of the composite material has macropores of average size between about 25 nm and about 1500 nm. In certain embodiments, the macroporous crosslinked gel has macropores of average size between about 50 nm and about 1000 nm. In certain embodiments, the macroporous crosslinked gel has macropores of average size of about 700 nm. In certain embodiments, the macroporous crosslinked gel has macropores of average size of about 300 nm.

In certain embodiments, the invention relates to any one of the above-mentioned fluid treatment devices or elements, wherein the macroporous cross-linked gel of the composite material is a hydrogel, a polyelectrolyte gel, a hydrophobic gel, a neutral gel, or a gel comprising functional groups. In certain embodiments, the invention relates to any one of the above-mentioned fluid treatment devices or elements, wherein the macroporous cross-linked gel of the composite material is a neutral or charged hydrogel; and the neutral or charged hydrogel is selected from the group consisting of cross-linked poly(vinyl alcohol), poly(acrylamide), poly(isopropylacrylamide), poly(vinylpyrrolidone), poly(hydroxymethyl acrylate), poly(ethylene oxide), copolymers of acrylic acid or methacrylic acid with acrylamide, isopropylacrylamide, or vinylpyrrolidone, copolymers of acrylamide-2-methyl-1-propanesulfonic acid with acrylamide, isopropylacrylamide, or vinylpyrrolidone, copolymers of (3-acrylamido-propyl) trimethylammonium chloride with acrylamide, isopropylacrylamide, or N-vinyl-pyrrolidone, and copolymers of diallyldimethylammonium chloride with acrylamide, isopropylacrylamide, or vinylpyrrolidone. In certain embodiments, the invention relates to any one of the above-mentioned fluid treatment devices or elements, wherein the macroporous cross-linked gel of the composite material is a polyelectrolyte gel; and the polyelectrolyte gel is selected from the group consisting of cross-linked poly(acrylamido-2-methyl-1-propanesulfonic acid) and its salts, poly(acrylic acid) and its salts, poly(methacrylic acid) and its salts, poly(styrenesulfonic acid) and its salts, poly(vinylsulfonic acid) and its salts, poly(alginic acid) and its salts, poly[(3-acrylamidopropyl)trimethylammonium] salts, poly(diallyldimethylammonium) salts, poly(4-vinyl-N-methylpyridinium) salts, poly(vinylbenzyl-N-trimethylammonium) salts, and poly(ethyleneimine) and its salts. In certain embodiments, the invention relates to any one of the above-mentioned fluid treatment devices or elements, wherein the macroporous cross-linked gel of the composite material is a hydrophobic gel; and the hydrophobic gel is selected from the group consisting of cross-linked polymers or copolymers of ethyl acrylate, n-butyl acrylate, propyl acrylate, octyl acrylate, dodecyl acrylate, octadecylacrylamide, stearyl acrylate, and styrene. In certain embodiments, the invention relates to any one of the above-mentioned fluid treatment devices or elements, wherein the macroporous cross-linked gel of the composite material is a neutral gel; and the neutral gel is selected from the group consisting of cross-linked polymers or copolymers of acrylamide, N,N-dimethylacrylamide, N-methacryloylacrylamide, N-methyl-N-vinylacetamide, and N-vinylpyrrolidone.

In certain embodiments, the invention relates to any one of the above-mentioned fluid treatment devices or elements, wherein the macroporous cross-linked gel of the composite material is a gel comprising functional groups. In certain embodiments, the macroporous cross-linked gel of the composite material comprises monomers, wherein the monomers comprise functional groups. In certain embodiments, the functional groups are thiols or protected thiols. In certain embodiments, the macroporous cross-linked gel comprises monomers, wherein the monomers are selected from the group consisting of allyl 3-mercaptopropionate thioacetate, (S-benzoyl-3-mercapto-2-hydroxypropyl)-2-methyl-2-propenoate, (S-2,2-dimethylpropanoyl-3-mercapto-2-hydroxypropyl)-2-methyl-2-propenoate, (S-acetyl-3-mercapto-2-acetylpropyl)-2-methyl-2-propenoate, (S-acetyl-3-mercapto-2-hydroxypropyl)-2-methyl-2-propenoate, (S-acetyl-3-mercapto-2-acetoacetylpropyl)-2-methyl-2-propenoate, (S-acetyl-3-mercapto-2-tetrahydropyranyl)-2-methyl-2-propenoate, (S-acetyl-3-mercapto-2-(2-methoxy-2-propoxy))-2-methyl-2-propenoate, (S-acetyl-2-mercapto-3-acetylpropyl)-2-methyl-2-propenoate, S-acetyl-(1-allyloxy-3-mercapto-2-hydroxypropane), S-benzoyl-(1-allyloxy-3-mercapto-2-hydroxypropane) and S-2,2-dimethylpropanoyl-(1-allyloxy-3-mercapto-2-hydroxypropane).

In certain embodiments, the invention relates to any one of the above-mentioned fluid treatment devices or elements, wherein the composite material comprises functional groups; and the functional groups are selected from the group consisting of amino acid ligands, antigen and antibody ligands, dye ligands, biological molecules, biological ions, and metal affinity ligands.

In certain embodiments, the invention relates to any one of the above-mentioned fluid treatment devices or elements, wherein the composite material comprises functional groups; and said functional groups are metal affinity ligands. In certain embodiments, the invention relates to any one of the above-mentioned fluid treatment devices or elements, wherein the composite material comprises functional groups; said functional groups are metal affinity ligands; and a plurality of metal ions are complexed to a plurality of said metal affinity ligands.

In certain embodiments, the invention relates to any one of the above-mentioned fluid treatment devices or elements, wherein the composite material comprises metal affinity ligands; and said metal affinity ligands are polydentate ligands.

In certain embodiments, the invention relates to any one of the above-mentioned fluid treatment devices or elements, wherein the composite material comprises metal affinity ligands; and said metal affinity ligands are octadentate, hexadentate, tetradentate, tridentate or bidentate ligands.

In certain embodiments, the invention relates to any one of the above-mentioned fluid treatment devices or elements, wherein the composite material comprises metal affinity ligands; and said metal affinity ligands are tetradentate ligands.

In certain embodiments, the invention relates to any one of the above-mentioned fluid treatment devices or elements, wherein the composite material comprises metal affinity ligands; and said metal affinity ligands are tridentate ligands.

In certain embodiments, the invention relates to any one of the above-mentioned fluid treatment devices or elements, wherein the composite material comprises metal affinity ligands; and said metal affinity ligands are bidentate ligands.

In certain embodiments, the invention relates to any one of the above-mentioned fluid treatment devices or elements, wherein the composite material comprises metal affinity ligands; and said metal affinity ligands are iminodicarboxylic acid ligands.

In certain embodiments, the invention relates to any one of the above-mentioned fluid treatment devices or elements, wherein the composite material comprises metal affinity ligands; and said metal affinity ligands are iminodiacetic acid ligands.

In certain embodiments, the invention relates to any one of the above-mentioned fluid treatment devices or elements, wherein the composite material comprises metal affinity ligands; and said metal affinity ligands are salts of iminodiacetic acid ligands.

Figure 24:
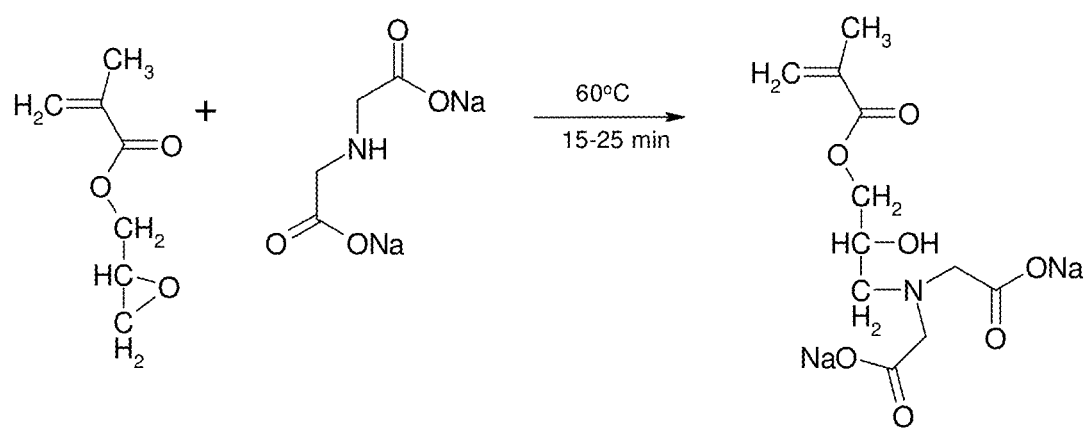
FIG. 24 depicts an exemplary synthetic scheme for incorporation of a metal affinity ligand into the membrane. In this case, the metal affinity ligand is the sodium salt of iminodiacetic acid ($IDA(Na)_2$).

In certain embodiments, the invention relates to any one of the above-mentioned fluid treatment devices or elements, wherein the composite material comprises metal affinity ligands; and said metal affinity ligands are sodium salts of iminodiacetic acid ligands. See, e.g., FIG. 24.

In certain embodiments, the invention relates to any one of the above-mentioned fluid treatment devices or elements, wherein the composite material comprises metal affinity ligands; and said metal affinity ligands are potassium salts of iminodiacetic acid ligands.

Figure 25:
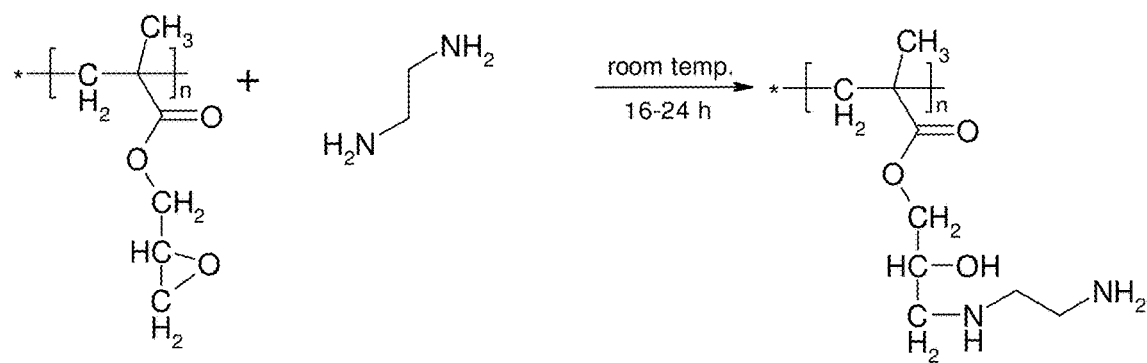
FIG. 25 depicts an exemplary synthetic scheme for incorporation of a metal affinity ligand into the membrane. In this case, the metal affinity ligand is ethylenediamine (EDA).

In certain embodiments, the invention relates to any one of the above-mentioned fluid treatment devices or elements, wherein the composite material comprises metal affinity ligands; and said metal affinity ligands comprise ethylenediamine moieties. See, e.g., FIG. 25.

Figure 26:
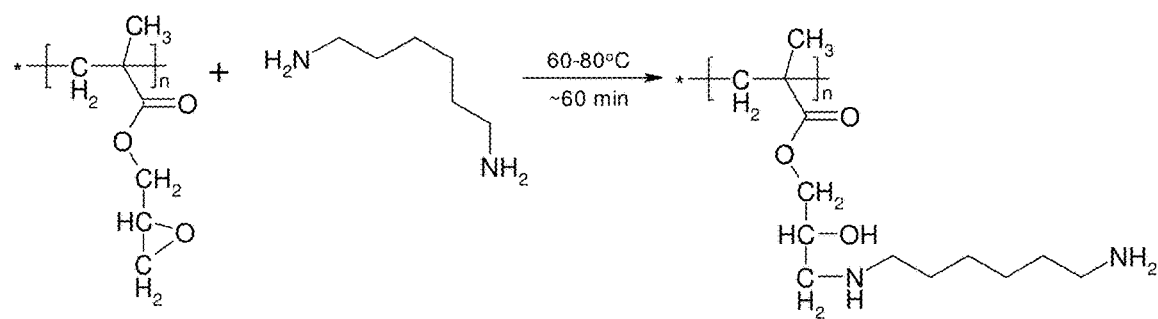
FIG. 26 depicts an exemplary synthetic scheme for incorporation of a metal affinity ligand into the membrane. In this case, the metal affinity ligand is hexamethylenediamine (HMDA).

In certain embodiments, the invention relates to any one of the above-mentioned fluid treatment devices or elements, wherein the composite material comprises metal affinity ligands; and said metal affinity ligands comprise hexamethylenediamine moieties. See, e.g., FIG. 26.

Figure 27:
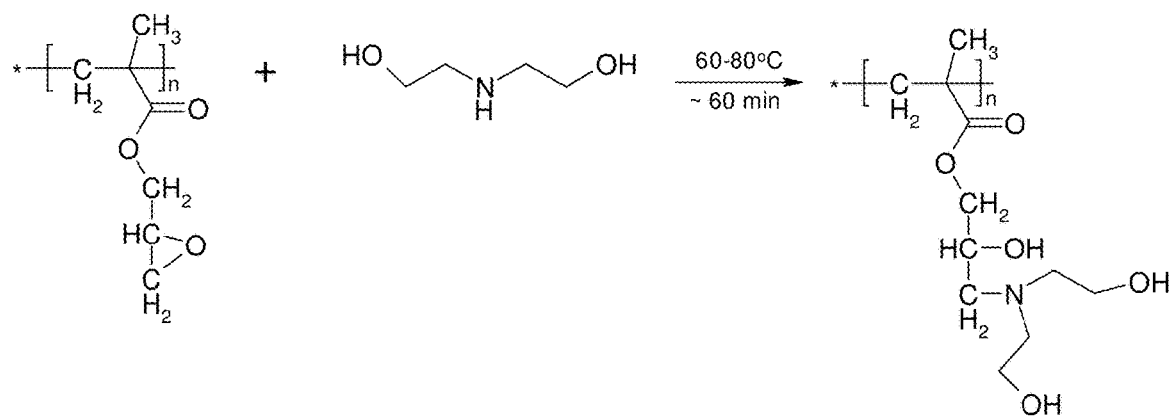
FIG. 27 depicts an exemplary synthetic scheme for incorporation of a metal affinity ligand into the membrane. In this case, the metal affinity ligand is diethanolamine.

In certain embodiments, the invention relates to any one of the above-mentioned fluid treatment devices or elements, wherein the composite material comprises metal affinity ligands; and said metal affinity ligands comprise diethanolamine moieties. See, e.g., FIG. 27.

Figure 28:
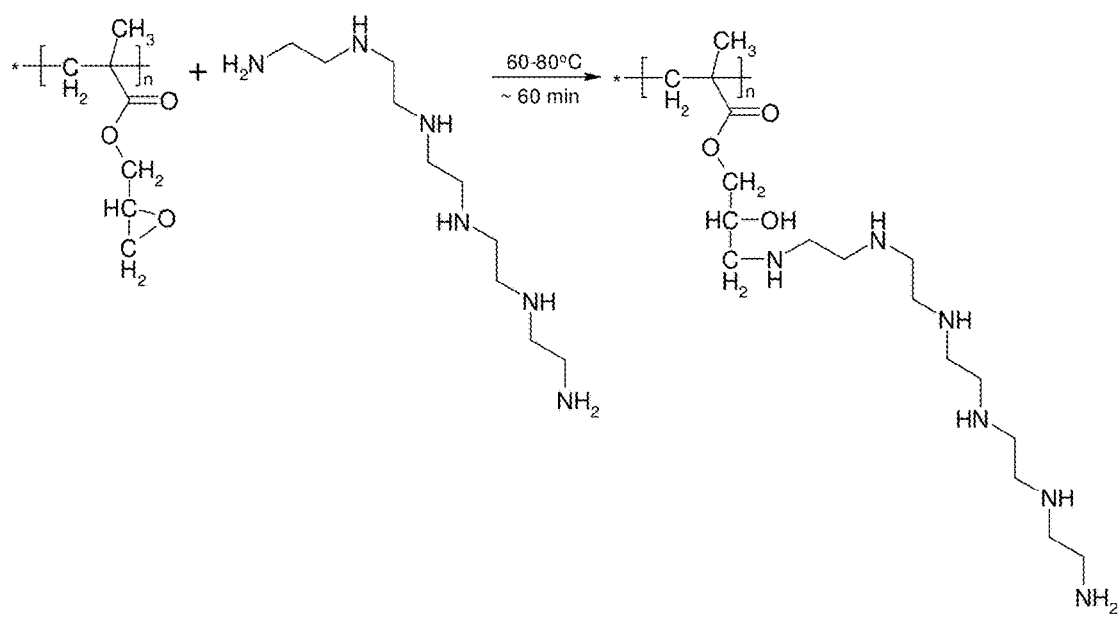
FIG. 28 depicts an exemplary synthetic scheme for incorporation of a metal affinity ligand into the membrane. In this case, the metal affinity ligand is pentaethylenehexamine (PEHA).

In certain embodiments, the invention relates to any one of the above-mentioned fluid treatment devices or elements, wherein the composite material comprises metal affinity ligands; and said metal affinity ligands comprise pentaethylenehexamine moieties. See, e.g., FIG. 28.

Figure 29:
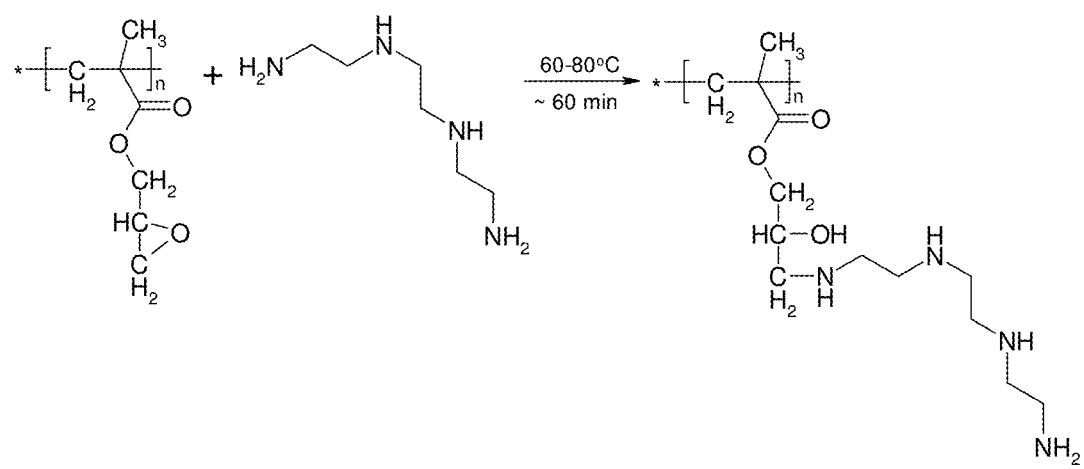
FIG. 29 depicts an exemplary synthetic scheme for incorporation of a metal affinity ligand into the membrane. In this case, the metal affinity ligand is triethylenetetramine (TETA).

In certain embodiments, the invention relates to any one of the above-mentioned fluid treatment devices or elements, wherein the composite material comprises metal affinity ligands; and said metal affinity ligands comprise triethylenetetramine moieties. See, e.g., FIG. 29.

Figure 30:
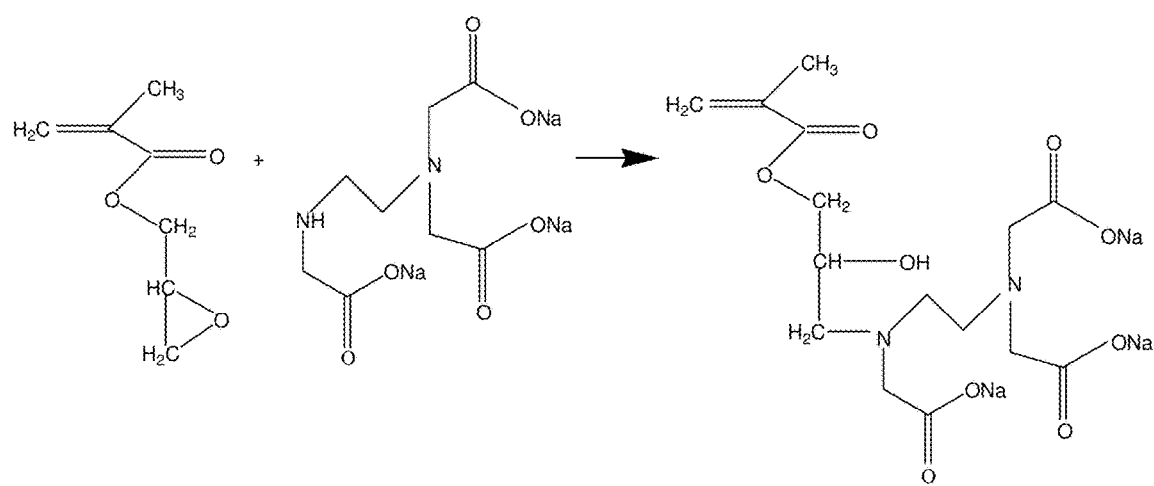
FIG. 30 depicts an exemplary synthetic scheme for incorporation of a metal affinity ligand into the membrane. In this case, the metal affinity ligand is the sodium salt of tris (carboxymethyl)ethylene diamine ($TED(Na)_3$).

In certain embodiments, the invention relates to any one of the above-mentioned fluid treatment devices or elements, wherein the composite material comprises metal affinity ligands; and said metal affinity ligands comprise tris(carboxymethyl)ethylene diamine. See, e.g., FIG. 30.

In certain embodiments, the invention relates to any one of the above-mentioned fluid treatment devices or elements, wherein the composite material comprises metal affinity ligands; and said metal affinity ligands comprise conjugate bases of carboxylic acids. In certain embodiments, the conjugate bases are available as salts. In certain embodiments, the conjugate bases are available as sodium salts or potassium salts. In certain embodiments, the conjugate bases are available as sodium salts. In certain embodiments, the conjugate bases are available as potassium salts.

In certain embodiments, the invention relates to any one of the above-mentioned fluid treatment devices or elements, wherein the composite material comprises metal affinity ligands complexed to a plurality of metal ions; and said metal ions are transition metal ions, lanthanide ions, poor metal ions or alkaline earth metal ions.

In certain embodiments, the invention relates to any one of the above-mentioned fluid treatment devices or elements, wherein the composite material comprises metal affinity ligands complexed to a plurality of metal ions; and said metal ions are selected from the group consisting of nickel, zirconium, lanthanum, cerium, manganese, titanium, cobalt, iron, copper, zinc, silver, gallium, platinum, palladium, lead, mercury, cadmium and gold.

In certain embodiments, the invention relates to any one of the above-mentioned fluid treatment devices or elements, wherein the composite material comprises metal affinity ligands complexed to a plurality of metal ions; and said metal ions are nickel or zirconium.

In certain embodiments, the invention relates to any one of the above-mentioned fluid treatment devices or elements, wherein the composite material comprises metal affinity ligands complexed to a plurality of metal ions; and said metal ions are nickel.

In certain embodiments, the invention relates to any one of the above-mentioned fluid treatment devices or elements, wherein the composite material comprises metal affinity ligands complexed to a plurality of metal ions; and said metal ions are zirconium.

In certain embodiments, the invention relates to any one of the above-mentioned fluid treatment devices or elements, wherein the composite material comprises metal affinity ligands complexed to a plurality of metal ions; said metal affinity ligands are octadentate, hexadentate, tetradentate, tridentate or bidentate ligands; and said metal ions are transition metal ions, lanthanide ions, poor metal ions or alkaline earth metal ions.

In certain embodiments, the invention relates to any one of the above-mentioned fluid treatment devices or elements, wherein the composite material comprises metal affinity ligands complexed to a plurality of metal ions; said metal affinity ligands are octadentate, hexadentate, tetradentate, tridentate or bidentate ligands; and said metal ions are selected from the group consisting of nickel, zirconium, lanthanum, cerium, manganese, titanium, cobalt, iron, copper, zinc, silver, gallium, platinum, palladium, lead, mercury, cadmium and gold.

In certain embodiments, the invention relates to any one of the above-mentioned fluid treatment devices or elements, wherein the composite material comprises metal affinity ligands complexed to a plurality of metal ions; said metal affinity ligands are octadentate, hexadentate, tetradentate, tridentate or bidentate ligands; and said metal ions are nickel or zirconium.

In certain embodiments, the invention relates to any one of the above-mentioned fluid treatment devices or elements, wherein the composite material comprises metal affinity ligands complexed to a plurality of metal ions; said metal affinity ligands are octadentate, hexadentate, tetradentate, tridentate or bidentate ligands; and said metal ions are nickel.

In certain embodiments, the invention relates to any one of the above-mentioned fluid treatment devices or elements, wherein the composite material comprises metal affinity ligands complexed to a plurality of metal ions; said metal affinity ligands are octadentate, hexadentate, tetradentate, tridentate or bidentate ligands; and said metal ions are zirconium.

In certain embodiments, the invention relates to any one of the above-mentioned fluid treatment devices or elements, wherein the composite material comprises metal affinity ligands complexed to a plurality of metal ions; said metal affinity ligands are tetradentate ligands; and said metal ions are transition metal ions, lanthanide ions, poor metal ions or alkaline earth metal ions.

In certain embodiments, the invention relates to any one of the above-mentioned fluid treatment devices or elements, wherein the composite material comprises metal affinity ligands complexed to a plurality of metal ions; said metal affinity ligands are tetradentate ligands; and said metal ions are selected from the group consisting of nickel, zirconium, lanthanum, cerium, manganese, titanium, cobalt, iron, copper, zinc, silver, gallium, platinum, palladium, lead, mercury, cadmium and gold.

In certain embodiments, the invention relates to any one of the above-mentioned fluid treatment devices or elements, wherein the composite material comprises metal affinity ligands complexed to a plurality of metal ions; said metal affinity ligands are tetradentate ligands; and said metal ions are nickel or zirconium.

In certain embodiments, the invention relates to any one of the above-mentioned fluid treatment devices or elements, wherein the composite material comprises metal affinity ligands complexed to a plurality of metal ions; said metal affinity ligands are tetradentate ligands; and said metal ions are nickel.

In certain embodiments, the invention relates to any one of the above-mentioned fluid treatment devices or elements, wherein the composite material comprises metal affinity ligands complexed to a plurality of metal ions; said metal affinity ligands are tetradentate ligands; and said metal ions are zirconium.

In certain embodiments, the invention relates to any one of the above-mentioned fluid treatment devices or elements, wherein the composite material comprises metal affinity ligands complexed to a plurality of metal ions; said metal affinity ligands are tridentate ligands; and said metal ions are transition metal ions, lanthanide ions, poor metal ions or alkaline earth metal ions.

In certain embodiments, the invention relates to any one of the above-mentioned fluid treatment devices or elements, wherein the composite material comprises metal affinity ligands complexed to a plurality of metal ions; said metal affinity ligands are tridentate ligands; and said metal ions are selected from the group consisting of nickel, zirconium, lanthanum, cerium, manganese, titanium, cobalt, iron, copper, zinc, silver, gallium, platinum, palladium, lead, mercury, cadmium and gold.

In certain embodiments, the invention relates to any one of the above-mentioned fluid treatment devices or elements, wherein the composite material comprises metal affinity ligands complexed to a plurality of metal ions; said metal affinity ligands are tridentate ligands; and said metal ions are nickel or zirconium.

In certain embodiments, the invention relates to any one of the above-mentioned fluid treatment devices or elements, wherein the composite material comprises metal affinity ligands complexed to a plurality of metal ions; said metal affinity ligands are tridentate ligands; and said metal ions are nickel.

In certain embodiments, the invention relates to any one of the above-mentioned fluid treatment devices or elements, wherein the composite material comprises metal affinity ligands complexed to a plurality of metal ions; said metal affinity ligands are tridentate ligands; and said metal ions are zirconium.

In certain embodiments, the invention relates to any one of the above-mentioned fluid treatment devices or elements, wherein the composite material comprises metal affinity ligands complexed to a plurality of metal ions; said metal affinity ligands are bidentate ligands; and said metal ions are transition metal ions, lanthanide ions, poor metal ions or alkaline earth metal ions.

In certain embodiments, the invention relates to any one of the above-mentioned fluid treatment devices or elements, wherein the composite material comprises metal affinity ligands complexed to a plurality of metal ions; said metal affinity ligands are bidentate ligands; and said metal ions are selected from the group consisting of nickel, zirconium, lanthanum, cerium, manganese, titanium, cobalt, iron, copper, zinc, silver, gallium, platinum, palladium, lead, mercury, cadmium and gold.

In certain embodiments, the invention relates to any one of the above-mentioned fluid treatment devices or elements, wherein the composite material comprises metal affinity ligands complexed to a plurality of metal ions; said metal affinity ligands are bidentate ligands; and said metal ions are nickel or zirconium.

In certain embodiments, the invention relates to any one of the above-mentioned fluid treatment devices or elements, wherein the composite material comprises metal affinity ligands complexed to a plurality of metal ions; said metal affinity ligands are bidentate ligands; and said metal ions are nickel.

In certain embodiments, the invention relates to any one of the above-mentioned fluid treatment devices or elements, wherein the composite material comprises metal affinity ligands complexed to a plurality of metal ions; said metal affinity ligands are bidentate ligands; and said metal ions are zirconium.

In certain embodiments, the invention relates to any one of the above-mentioned fluid treatment devices or elements, wherein the composite material comprises metal affinity ligands complexed to a plurality of metal ions; said metal affinity ligands are iminodicarboxylic acid ligands; and said metal ions are transition metal ions, lanthanide ions, poor metal ions or alkaline earth metal ions.

In certain embodiments, the invention relates to any one of the above-mentioned fluid treatment devices or elements, wherein the composite material comprises metal affinity ligands complexed to a plurality of metal ions; said metal affinity ligands are iminodicarboxylic acid ligands; and said metal ions are selected from the group consisting of nickel, zirconium, lanthanum, cerium, manganese, titanium, cobalt, iron, copper, zinc, silver, gallium, platinum, palladium, lead, mercury, cadmium and gold.

In certain embodiments, the invention relates to any one of the above-mentioned fluid treatment devices or elements, wherein the composite material comprises metal affinity ligands complexed to a plurality of metal ions; said metal affinity ligands are iminodicarboxylic acid ligands; and said metal ions are nickel or zirconium.

In certain embodiments, the invention relates to any one of the above-mentioned fluid treatment devices or elements, wherein the composite material comprises metal affinity ligands complexed to a plurality of metal ions; said metal affinity ligands are iminodicarboxylic acid ligands; and said metal ions are nickel.

In certain embodiments, the invention relates to any one of the above-mentioned fluid treatment devices or elements, wherein the composite material comprises metal affinity ligands complexed to a plurality of metal ions; said metal affinity ligands are iminodicarboxylic acid ligands; and said metal ions are zirconium.

In certain embodiments, the invention relates to any one of the above-mentioned fluid treatment devices or elements, wherein the composite material comprises metal affinity ligands complexed to a plurality of metal ions; said metal affinity ligands are iminodiacetic acid ligands; and said metal ions are transition metal ions, lanthanide ions, poor metal ions or alkaline earth metal ions.

In certain embodiments, the invention relates to any one of the above-mentioned fluid treatment devices or elements, wherein the composite material comprises metal affinity ligands complexed to a plurality of metal ions; said metal affinity ligands are iminodiacetic acid ligands; and said metal ions are selected from the group consisting of nickel, zirconium, lanthanum, cerium, manganese, titanium, cobalt, iron, copper, zinc, silver, gallium, platinum, palladium, lead, mercury, cadmium and gold.

In certain embodiments, the invention relates to any one of the above-mentioned fluid treatment devices or elements, wherein the composite material comprises metal affinity ligands complexed to a plurality of metal ions; said metal affinity ligands are iminodiacetic acid ligands; and said metal ions are nickel or zirconium.

In certain embodiments, the invention relates to any one of the above-mentioned fluid treatment devices or elements, wherein the composite material comprises metal affinity ligands complexed to a plurality of metal ions; said metal affinity ligands are iminodiacetic acid ligands; and said metal ions are nickel.

In certain embodiments, the invention relates to any one of the above-mentioned fluid treatment devices or elements, wherein the composite material comprises metal affinity ligands complexed to a plurality of metal ions; said metal affinity ligands are iminodiacetic acid ligands; and said metal ions are zirconium.

In certain embodiments, the invention relates to any one of the above-mentioned fluid treatment devices or elements, wherein the composite material comprises functional groups; and the functional groups are biological molecules or biological ions. In certain embodiments, the biological molecules or biological ions are selected from the group consisting of albumins, lysozyme, viruses, cells, γ-globulins of human and animal origins, immunoglobulins of both human and animal origins, proteins of recombinant or natural origin including, polypeptides of synthetic or natural origin, interleukin-2 and its receptor, enzymes, monoclonal antibodies, antigens, lectins, bacterial immunoglobulin-binding proteins, trypsin and its inhibitor, cytochrome C, myoglobulin, recombinant human interleukin, recombinant fusion protein, Protein A, Protein G, Protein L, Peptide H, nucleic acid derived products, DNA of either synthetic or natural origin, and RNA of either synthetic or natural origin.

In certain embodiments, the invention relates to any one of the above-mentioned fluid treatment devices or elements, wherein the composite material comprises Protein A. Protein A is a 40-60 kDa MSCRAMM surface protein originally found in the cell wall of the bacteria *Staphylococcus aureus*. It is encoded by the spa gene and its regulation is controlled by DNA topology, cellular osmolarity, and a two-component system called ArlS-ArlR. It has found use in biochemical research because of its ability to bind immunoglobulins. It binds proteins from many of mammalian species, most notably IgGs. It binds with the Fc region of immunoglobulins through interaction with the heavy chain. The result of this type of interaction is that, in serum, the bacteria will bind IgG molecules in the wrong orientation (in relation to normal antibody function) on their surface which disrupts opsonization and phagocytosis. It binds with high affinity to human IgG1 and IgG2 as well as mouse IgG2a and IgG2b. Protein A binds with moderate affinity to human IgM, IgA and IgE as well as to mouse IgG3 and IgG1. It does not react with human IgG3 or IgD, nor will it react to mouse IgM, IgA or IgE.

In certain embodiments, the invention relates to any one of the above-mentioned fluid treatment devices or elements, wherein the macroporous crosslinked gel of the composite material comprises a macromonomer. In certain embodiments, the macromonomer is selected from the group consisting of poly(ethylene glycol) acrylate and poly(ethylene glycol) methacrylate.

In certain embodiments, the invention relates to any one of the above-mentioned fluid treatment devices or elements, wherein the macroporous cross-linked gel of the composite material is cross-linked by N,N-methylenebisacrylamide or a polyfunctional macromonomer. In certain embodiments, the macroporous cross-linked gel of the composite material is cross-linked by a polyfunctional macromonomer; and the polyfunctional macromonomer is selected from the group consisting of poly(ethylene glycol) diacrylate and poly(ethylene glycol) dimethacrylate. In certain embodiments, the invention relates to any one of the above-mentioned fluid treatment devices or elements, wherein the macroporous cross-linked gel of the composite material is cross-linked by N,N-methylenebisacrylamide.

In certain embodiments, the invention relates to any one of the above-mentioned fluid treatment devices or elements, wherein the macroporous cross-linked gel of the composite material is a positively charged hydrogel comprising a co-polymer of (3-acrylamidopropyl)trimethylammonium chloride (APTAC) and N-(hydroxymethyl)acrylamide cross-linked by N,N'-methylenebisacrylamide.

In certain embodiments, the invention relates to any one of the above-mentioned fluid treatment devices or elements, wherein the composite material is a membrane; and the macroporous cross-linked gel bears charged moieties.

In certain embodiments, the invention relates to any one of the above-mentioned fluid treatment devices or elements, wherein the composite material is a membrane for use as a filter in size exclusion separation.

In certain embodiments, the fluid treatment devices or elements of the invention comprise any one of the above-mentioned composite materials, wherein the composite materials comprise negatively-charged moieties. Negatively-charged membranes repel foulants at the membrane surface resulting in higher flux, easier cleanings, and lower system costs.

In certain embodiments, the fluid treatment devices or elements of the invention comprise any one of the above-mentioned composite materials, wherein the composite materials are hydrophilic in nature. Foulants are typically hydrophobic species.

In certain embodiments, the invention relates to any one of the above-mentioned fluid treatment devices or elements, wherein the support member of the composite material consists essentially of polymeric material in the form of a membrane that has a thickness of from about 10 µm to about 500 µm and comprises pores of average size between about 0.1 to about 25 µm.

In certain embodiments, the invention relates to any one of the above-mentioned fluid treatment devices or elements, wherein the support member of the composite material consists essentially of a polyolefin.

In certain embodiments, the invention relates to any one of the above-mentioned fluid treatment devices or elements, wherein the support member of the composite material comprises a polymeric material selected from the group consisting of polysulfones, polyethersulfones, polyphenyleneoxides, polycarbonates, polyesters, cellulose and cellulose derivatives.

In certain embodiments, the invention relates to any one of the above-mentioned fluid treatment devices or elements, wherein the support member of the composite material consists essentially of polymeric material in the form of a fibrous fabric that has a thickness of from about 10 µm to about 2000 µm and comprises pores of average size from about 0.1 to about 25 µm.

In certain embodiments, the invention relates to any one of the above-mentioned fluid treatment devices or elements, wherein the support member of the composite material comprises a stack of 2 to 10 separate support members.

In certain embodiments, the invention relates to any one of the above-mentioned fluid treatment devices or elements, wherein the composite materials are disk-shaped, thereby forming cut disk membranes. In certain embodiments, the cut disk membranes are from about 5 mm in diameter to about 100 mm in diameter. In certain embodiments, the cut disk membranes are from about 10 mm in diameter to about 75 mm in diameter. In certain embodiments, the cut disk membranes are from about 15 mm in diameter to about 55 mm in diameter. In certain embodiments, the cut disk membranes are about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 mm in diameter. In certain embodiments, the cut disk membranes are about 18 mm in diameter. In certain embodiments, the cut disk membranes are about 25 mm in diameter. In certain embodiments, the cut disk membranes are about 50 mm in diameter. In certain embodiments, the cut disk membranes are made by simply cutting from sheets of composite material.

Exemplary Methods

In certain embodiments, the invention relates to a method comprising the step of:
 contacting a first fluid comprising a substance with a composite material in any one of the above-mentioned fluid treatment devices, thereby adsorbing or absorbing the substance onto the composite material.

In certain embodiments, the invention relates to any one of the above-mentioned methods, further comprising the step of
 placing the first fluid in an inlet of the fluid treatment device.

In certain embodiments, the invention relates to any one of the above-mentioned methods, wherein the first fluid is passed along a fluid flow path substantially perpendicular to the pores of the support member.

In certain embodiments, the invention relates to any one of the above-mentioned methods, further comprising the step of
 contacting a second fluid with the substance adsorbed or absorbed onto the composite material, thereby releasing the substance from the composite material.

In certain embodiments, the invention relates to any one of the above-mentioned methods, wherein the second fluid is passed through the macropores of the composite material, thereby releasing the substance from the composite material.

In certain embodiments, the invention relates to any one of the above-mentioned methods, wherein the second fluid is passed along the fluid flow path substantially perpendicular to the pores of the support member, thereby releasing the substance from the composite material.

In certain embodiments, the invention relates to any one of the above-mentioned methods, wherein the substance is separated based on size exclusion.

In certain embodiments, the invention relates to any one of the above-mentioned methods, wherein the macroporous gel displays a specific interaction for the substance.

In certain embodiments, the invention relates to any one of the above-mentioned methods, wherein the specific interactions are electrostatic interactions, affinity interactions, or hydrophobic interactions.

In certain embodiments, the invention relates to any one of the above-mentioned methods, wherein the specific interactions are electrostatic interactions, the composite material bears charges on the macroporous gel; the substance is charged; and the substance is separated based on Donnan exclusion.

In certain embodiments, the invention relates to any one of the above-mentioned methods, wherein the first fluid is a suspension of cells or a suspension of aggregates.

In certain embodiments, the invention relates to any one of the above-mentioned methods, wherein the substance is a biological molecule or biological ion.

In certain embodiments, the invention relates to any one of the above-mentioned methods, wherein the biological molecule or biological ion is selected from the group consisting of albumins, lysozyme, viruses, cells, γ-globulins of human and animal origins, immunoglobulins of both human and animal origins, proteins of recombinant or natural origin including, polypeptides of synthetic or natural origin, interleukin-2 and its receptor, enzymes, monoclonal antibodies, trypsin and its inhibitor, cytochrome C, myoglobulin, recombinant human interleukin, recombinant fusion protein, nucleic acid derived products, DNA of either synthetic or natural origin, and RNA of either synthetic or natural origin.

In certain embodiments, the invention relates to any one of the above-mentioned methods, wherein the biological molecule or biological ion is a protein; and the protein comprises exposed amino acid residues selected from the group consisting of Glu, Asp, Try, Arg, Lys, Met, and His.

In certain embodiments, the invention relates to any one of the above-mentioned methods, wherein the biological molecule or biological ion is a protein; and the protein comprises exposed His amino acid residues.

In certain embodiments, the invention relates to any one of the above-mentioned methods, wherein the biological molecule or biological ion is a monoclonal antibody.

In certain embodiments, the invention relates to any one of the above-mentioned methods, wherein the substance is a metal-containing particle, or a metal-containing ion.

In certain embodiments, the invention relates to any one of the above-mentioned methods, wherein the metal-containing particle or metal-containing ion comprises a transition metal, a lanthanide, a poor metal, or an alkaline earth metal.

In certain embodiments, the invention relates to any one of the above-mentioned methods, wherein the metal-containing particle or metal-containing ion comprises a metal selected from the group consisting of nickel, zirconium, lanthanum, cerium, manganese, titanium, cobalt, iron, copper, zinc, silver, gallium, platinum, palladium, lead, mercury, cadmium and gold.

In certain embodiments, the invention relates to any one of the above-mentioned methods, wherein the first fluid is waste water.

In certain embodiments, the invention relates to any one of the above-mentioned methods, wherein the first fluid is waste water from ore refining, or seawater.

In certain embodiments, the invention relates to any one of the above-mentioned methods, wherein the substance is lead or mercury.

In certain embodiments, the invention relates to any one of the above-mentioned methods, wherein the substance is platinum, palladium, copper, gold, or silver.

In certain embodiments, the invention relates to any one of the above-mentioned methods, wherein the fluid is waste water; and the metal-containing particle or metal-containing ion comprises lead or mercury.

In certain embodiments, the invention relates to any one of the above-mentioned methods, wherein the first fluid is waste water from ore refining; and the metal-containing particle or metal-containing ion comprises lead or mercury.

In certain embodiments, the invention relates to any one of the above-mentioned methods, wherein the first fluid is seawater; and the metal-containing particle or metal-containing ion comprises platinum, palladium, copper, gold, or silver.

In certain embodiments, the invention relates to any one of the above-mentioned methods, wherein the first fluid comprises egg white.

In certain embodiments, the invention relates to any one of the above-mentioned methods, wherein the first fluid comprises egg white; and the substance is lysozyme.

In certain embodiments, the invention relates to a method in which, in tangential flow separation mode, no pre-processing of the raw reaction mixtures is required due to the high specificity of the composite materials in the devices of the present invention. In certain embodiments, the invention relates to a method in which separations can be carried out on a large scale. In certain embodiments, the invention relates to a method in which separations can be carried out in a shorter amount of time. In certain embodiments, the invention relates to a method in which the devices have a high binding capacity.

In certain embodiments, the invention relates to a method that comprises two steps—collecting the desired substance onto the composite material and harvesting the desired substance from the composite material. In certain embodiments, the first step is run in tangential separation mode. In certain embodiments, the first step is run in tangential separation mode and the second step is run in direct filtration mode with a second fluid.

In certain embodiments, the invention relates to a method of separating a substance from a fluid, comprising the step of:

placing the fluid in contact with a composite material in any one of the above-mentioned fluid treatment devices, thereby adsorbing or absorbing the substance to the composite material.

In certain embodiments, the invention relates to a method of separating a substance from a fluid, comprising the step of:

placing the fluid in an inlet of any one of the above-mentioned fluid treatment devices, thereby adsorbing or absorbing the substance to the composite material and producing a permeate; and collecting the permeate from an outlet of the fluid treatment device.

In certain embodiments, the invention relates to the above-mentioned method, wherein the fluid is passed over the surface of the composite material; and the substance is adsorbed or absorbed onto the surface of the composite material.

In certain embodiments, the invention relates to the above-mentioned method, wherein the fluid is passed through the macropores of the composite material; and the substance is adsorbed or absorbed within the macropores of the composite material.

In certain embodiments, the invention relates to a method of separating a substance from a fluid, comprising the step of:

placing the fluid in an inlet of any one of the above-mentioned fluid treatment devices, thereby adsorbing or absorbing the substance to the composite material;

collecting the permeate from an outlet of the fluid treatment device;

placing a second fluid in the inlet of the fluid treatment device, thereby releasing the substance from the composite material.

In certain embodiments, the invention relates to the above-mentioned method, wherein the fluid is passed over the surface of the composite material; the substance is adsorbed or absorbed onto the surface of the composite material; and the second fluid is passed through the macropores of the composite material, thereby releasing the substance from the composite material.

In certain embodiments, the invention relates to the above-mentioned method, wherein the fluid is passed over the surface of the composite material; the substance is adsorbed or absorbed onto the surface of the composite material; and the second fluid is passed over the surface of the composite material, thereby releasing the substance from the surface of the composite material.

In certain embodiments, the invention relates to the above-mentioned method, wherein the fluid is passed through the macropores of the composite material; the substance is adsorbed or absorbed within the macropores of the composite material; and the second fluid is passed over the surface of the composite material, thereby releasing the substance from the composite material.

In certain embodiments, the invention relates to the above-mentioned method, wherein the fluid is passed through the macropores of the composite material; the substance is adsorbed or absorbed within the macropores of the composite material; and the second fluid is passed through the macropores of the composite material, thereby releasing the substance from the composite material.

In certain embodiments, the invention relates to any one of the above-mentioned methods, wherein the substance is radioactive.

In certain embodiments, the invention relates to a method of separating a substance from a fluid, comprising the steps of:

placing the fluid in an inlet of any one of the above-mentioned fluid treatment devices, thereby adsorbing or absorbing the substance to the composite material and producing a permeate; and collecting the permeate from an outlet of the fluid treatment device, wherein the fluid comprises egg white; and the substance is lysozyme.

In certain embodiments, the invention relates to the above-mentioned method, wherein the fluid is passed over the surface of the fluid treatment element; and the substance is adsorbed or absorbed onto the surface of the fluid treatment element.

In certain embodiments, the invention relates to a method of separating a substance from a first fluid, comprising the steps of:

placing the first fluid in an inlet of any one of the above-mentioned fluid treatment devices, thereby adsorbing or absorbing the substance to the composite material;

collecting the permeate from an outlet of the fluid treatment device;

placing a second fluid in the inlet of the fluid treatment device, thereby releasing the substance from the composite material, wherein the first fluid comprises egg white; and the substance is lysozyme.

In certain embodiments, the invention relates to the above-mentioned method, wherein the fluid is passed over the surface of the fluid treatment element; the substance is adsorbed or absorbed onto the surface of the fluid treatment element; and the second fluid is passed through the macropores of the fluid treatment element, thereby releasing the substance from the macropores. In certain embodiments, the invention relates to the above-mentioned method, wherein the fluid is passed over the surface of the fluid treatment element; the substance is adsorbed or absorbed onto the surface of the fluid treatment element; and the second fluid is passed over the surface of the fluid treatment element, thereby releasing the substance from the surface of the fluid treatment element.

EXEMPLIFICATION

The invention now being generally described, it will be more readily understood by reference to the following examples, which are included merely for purposes of illustration of certain aspects and embodiments of the present invention, and are not intended to limit the invention.

EXAMPLE 1

Dead-End versus Cross-Flow Modes for Viral Capture

An example of the improvement of cross-flow technology versus dead-end technology can be realized when the two modes are compared directly to each other. FIG. 1 shows two experiments in which a specific device was run as a dead-end and as cross-flow device. The material of interest is a virus. In both cases, the capture of the cross-flow device exceeded the dead-end version, as indicated by the amount to the pure target material capture after washing and elution.

EXAMPLE 2

Chromatographic Capture and Harvest: Elution of Ovalbumin and Lysozyme

Figure 2:
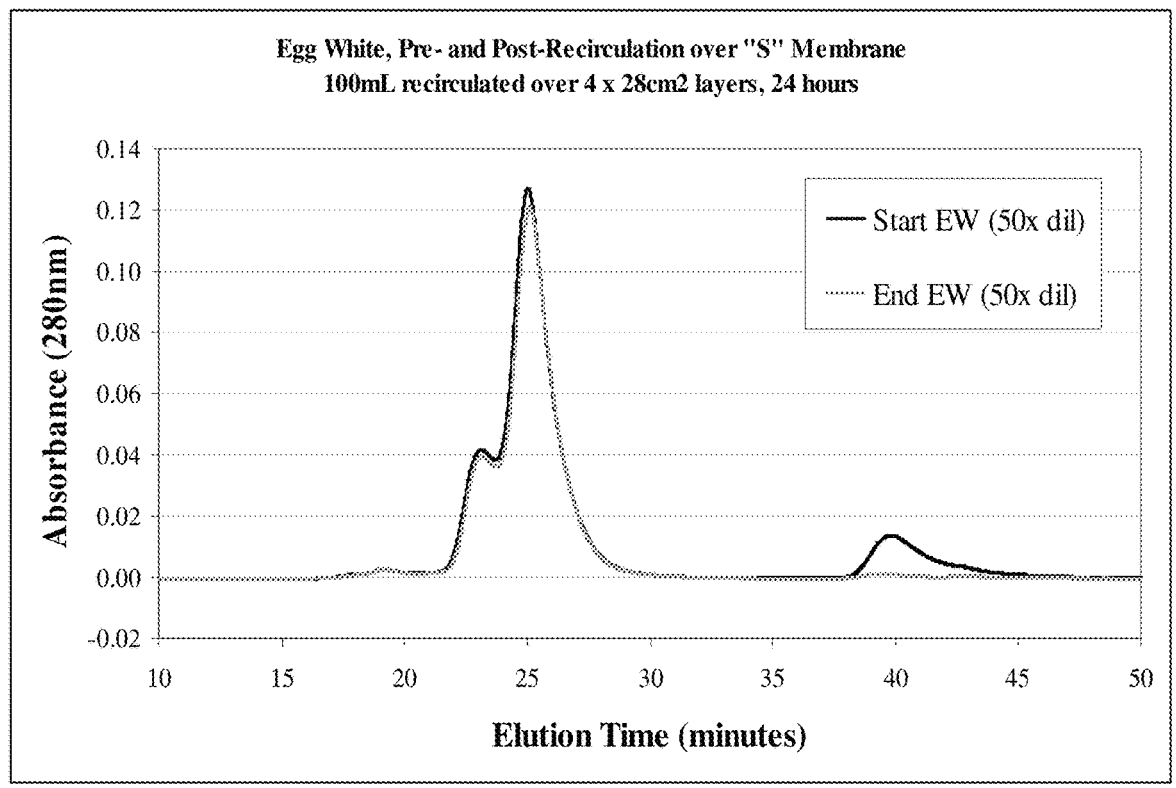
FIG. 2 depicts a chromatogram from the elution of a mixture proteins (ovalbumin and lysozyme) captured directly from unprocessed egg whites using ion-exchange membranes in cross-flow mode. The results demonstrate that proteins can be selectively removed from an unprocessed, highly viscous feed stream.
Figure 3:
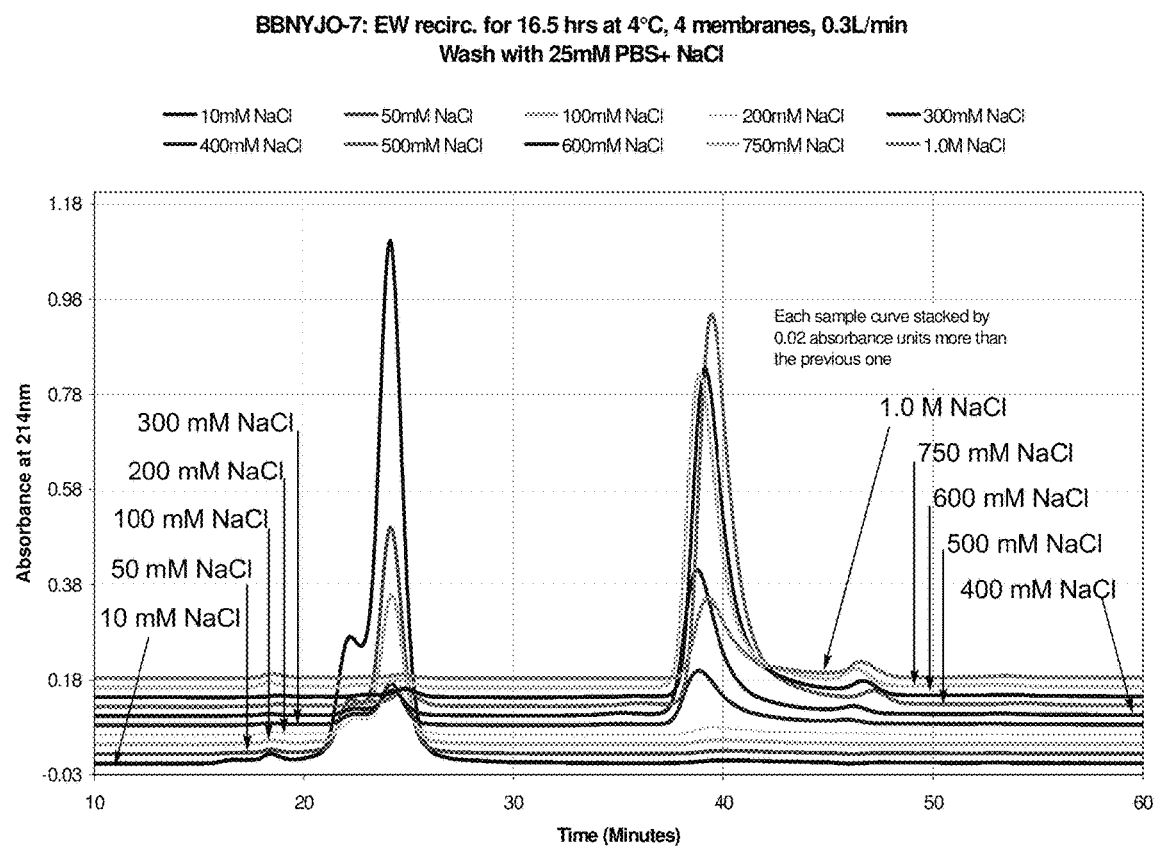
FIG. 3 depicts chromatograms of eluent fluids from egg white-loaded ion-exchange membranes. Curves show selectivity of elution, based on buffer (saline solution) selection. This series of curves demonstrates the ability selectively to separate (i.e., chromatographically) captured target materials in high purity, or as mixtures essentially free from other constituents.

The membrane can selectively adsorb two protein materials from the feed stream and then, through the use of an altering buffer fluid, selectively elute the target bio-molecules. FIGS. 2 and 3 illustrate this effect. The initial feed stream of egg white was exposed to a membrane surface in cross-flow mode. Once the feed stream was removed and the membrane washed, both Ovalbumin and lysozyme were found adhered to the membrane (FIG. 2). Under specific buffer conditions, the proteins were selectively eluted (FIG. 3), which demonstrates the chromatographic nature of the membrane in cross-flow mode.

EXAMPLE 3

Figure 4:
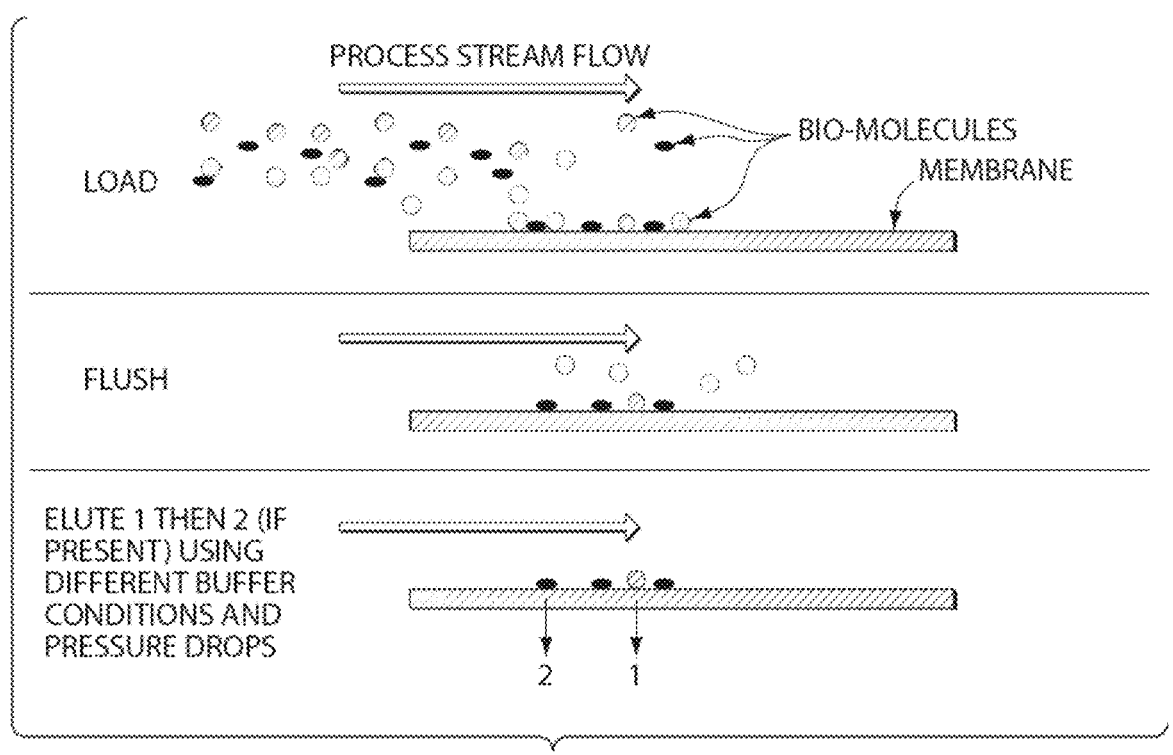
FIG. 4 depicts a schematic of the cross-flow and capture steps (top and middle), and a trans-membrane collection step (bottom).

Orthogonal Two-Step Capture and Harvest
    See FIG. 4.

EXAMPLE 4

Device Design: Wrap Design Data and Schematics

Figure 5:
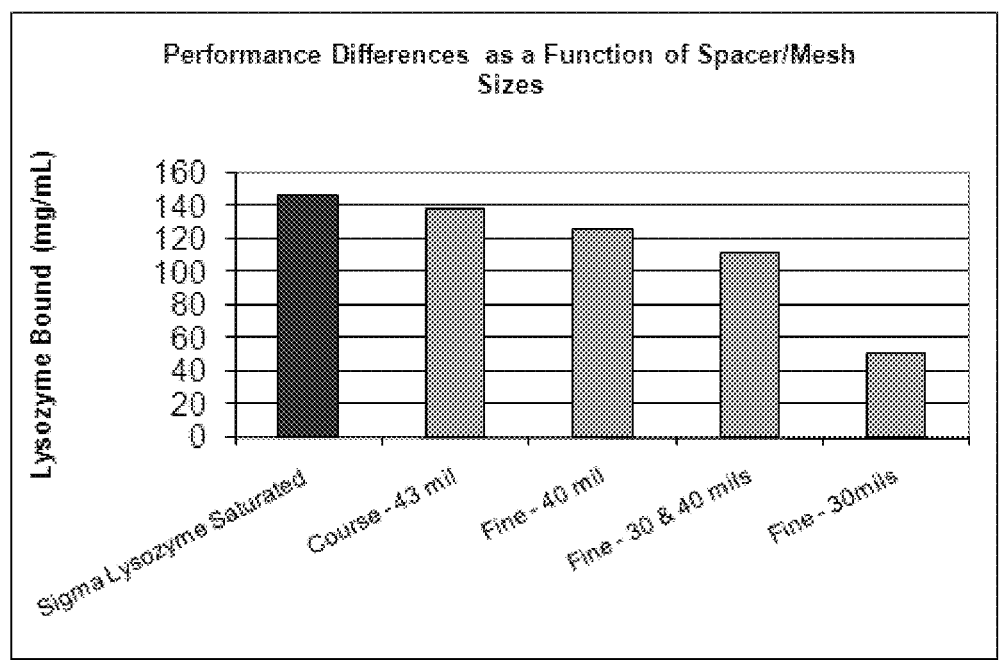
FIG. 5 depicts the effects of wrap design on device performance showing that coarse mesh spacers lead to improved performance in separating lysozyme from egg white using ion-exchange membrane.
Figure 6:
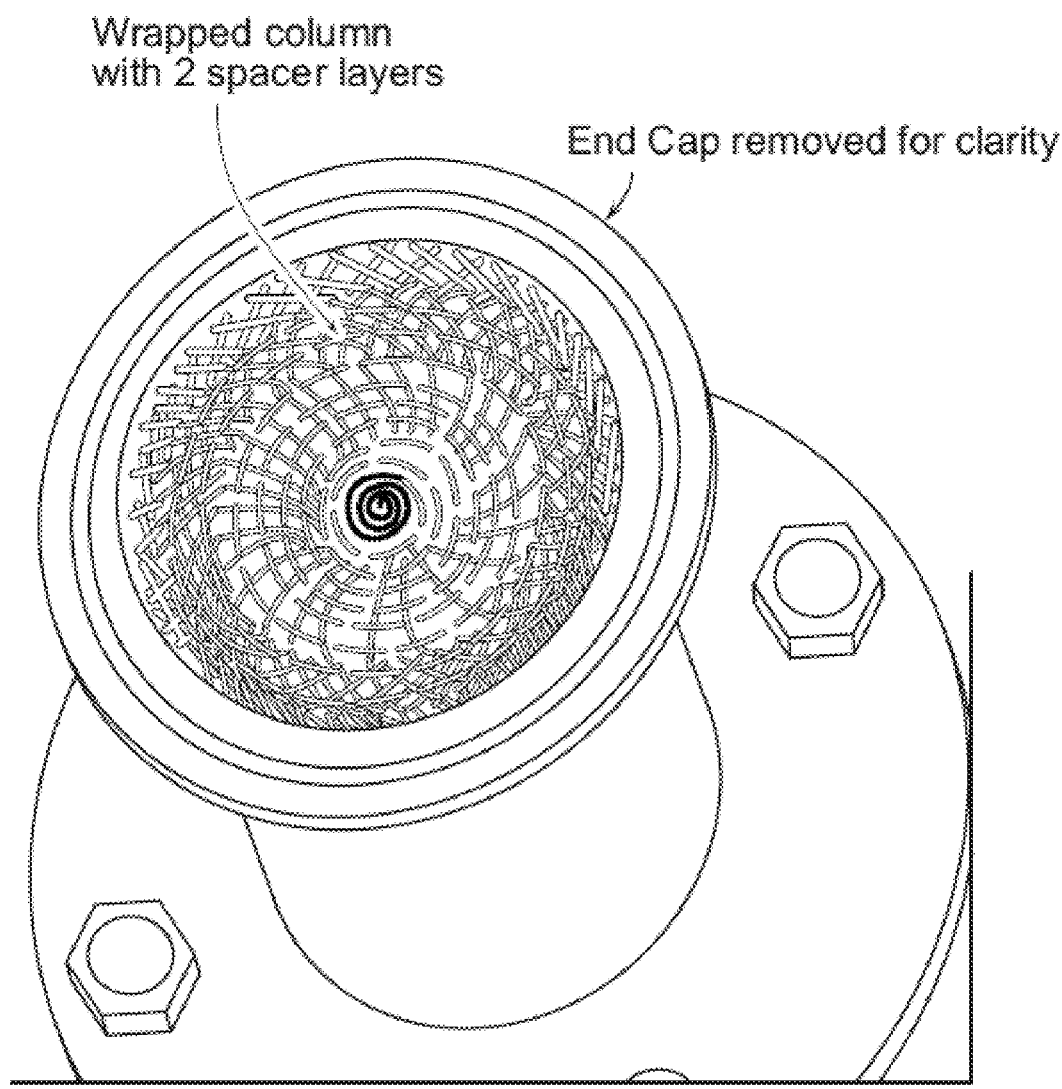
FIG. 6 depicts a wrapped column device inserted into a housing. Inlet cap not shown for clarity.

The effect of selecting an optimal spacer material in a simple wrapped design was observed and is depicted in FIG. 5. In this design, a roll was made by layering the necessary membrane sheet between two identical spacer sheets and rolling the multi-layered structure into a column. This column was then placed into a metal tube housing that was fitted with end-caps which have both an inlet(s) and outlet(s) attached (FIG. 6). The larger spacer material and loose-wind structure enabled the ideal cross-flow or tangential-flow adsorption. Importantly, this design eliminated any direct trans-membrane flow, as the process fluid was run on either side of the membrane. Thus, the improvements stemmed, at least partially, from the low shear environment. The purified lysozyme control was run on the device and was used to represent 100% or maximum adsorption of the target species. The remaining data were generated directly from process fluid streams (egg whites). In this embodiment, the spacer layer materials on either side of the membrane were identical but there is no requirement for this symmetry and the "roll" could have differing layers or one layer could be completely absent.

EXAMPLE 5

Device Design: Cassettes

Figure 7:
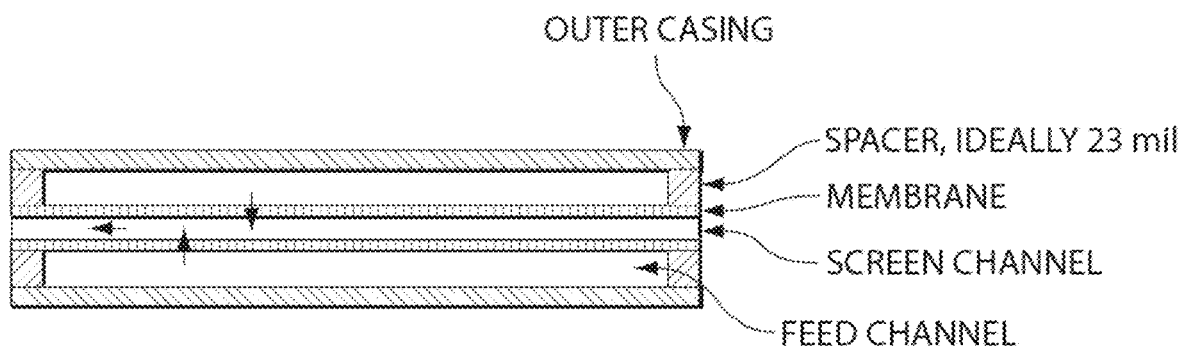
FIG. 7 depicts a simplified cross-section of a cassette showing trans-membrane flow of target material as indicated by arrows. Harvesting could also be accomplished by cross-flow, if required, using a fluid that selectively eluted the bound target materials.
Figure 8:
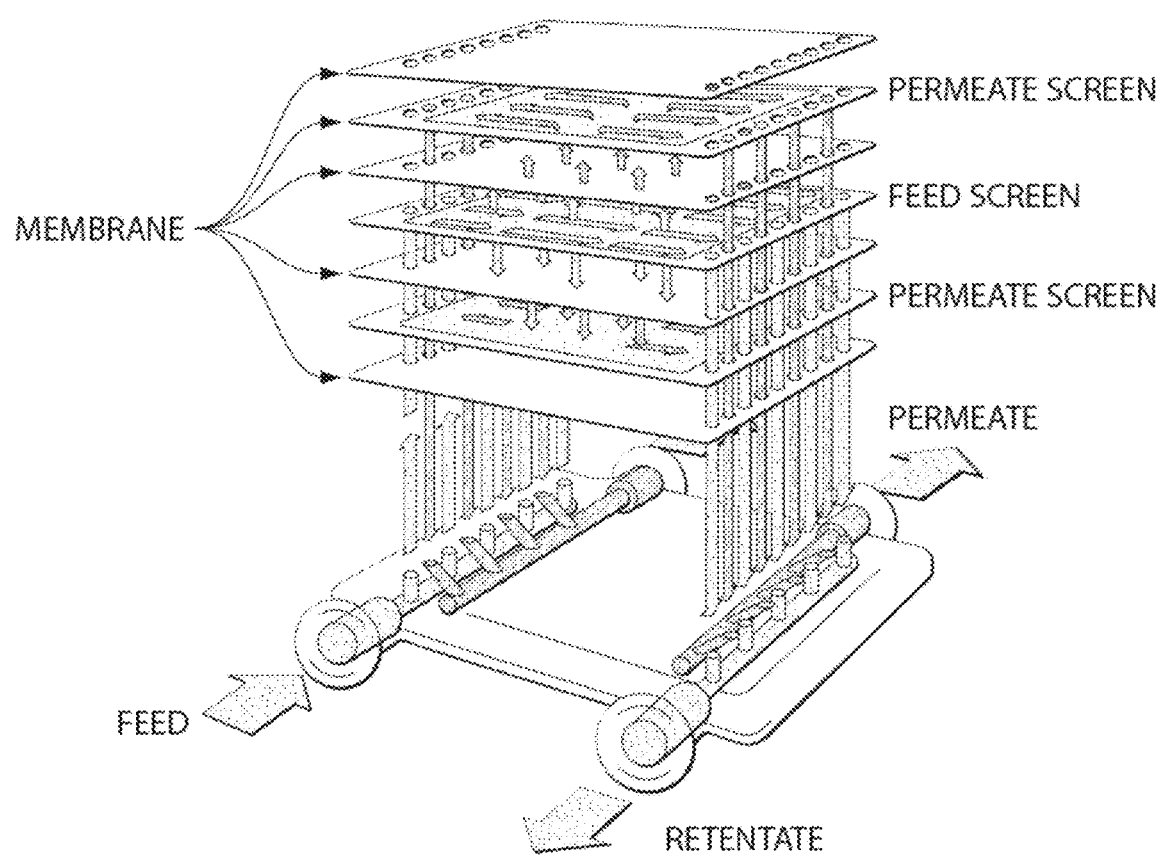
FIG. 8 depicts a schematic illustration of a typical cassette design. Flow is shown with trans-membrane harvesting that is occurring simultaneously with a flowing feed stream.
Figure 9:
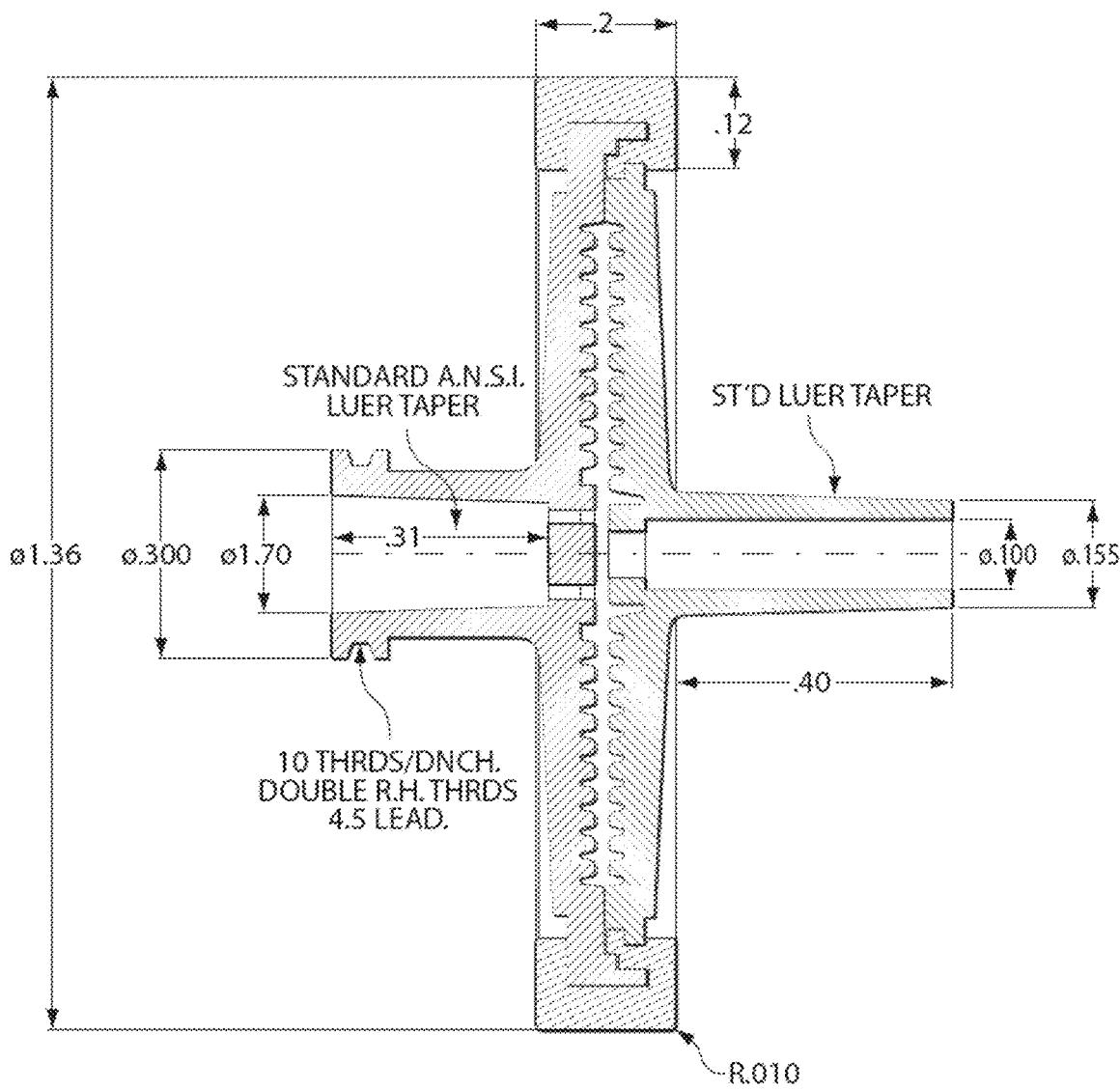
FIG. 9 depicts a cross-section of a disposable or semi-disposable housing for a 25 mm syringe column comprising a disk-shaped filtration membrane for lab-scale use.
Figure 10:
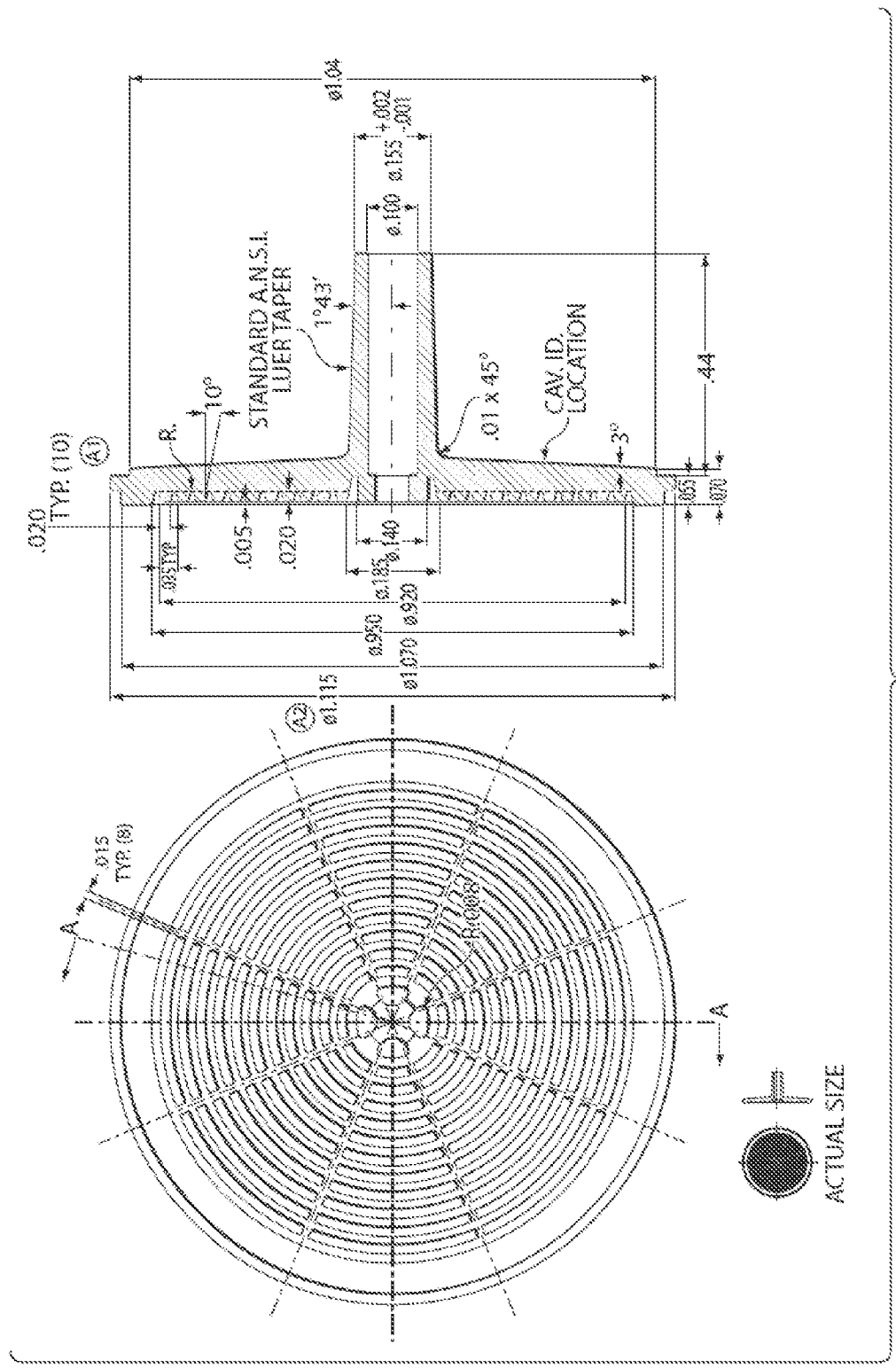
FIG. 10 depicts top view (top left), side view (right), and actual size views (bottom left) of the outlet half of the syringe tip filters for use in the housing shown in FIG. 9 and FIG. 11. All units in the drawings are in inches.
Figure 11:
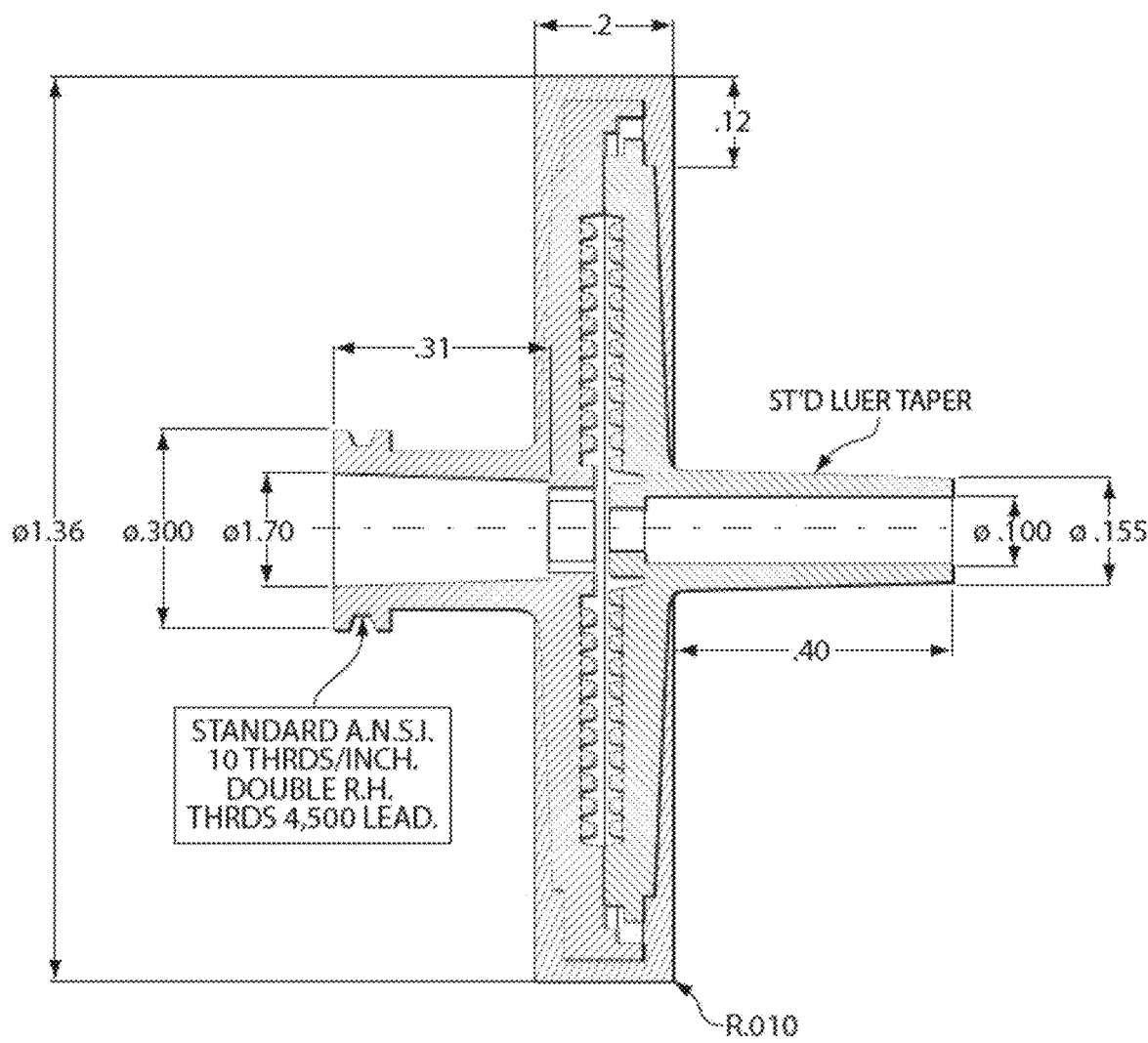
FIG. 11 depicts a cross-section of the disposable or semi-disposable housing for a 25 mm syringe column comprising a disk-shaped filtration membrane for lab-scale use.
Figure 12:
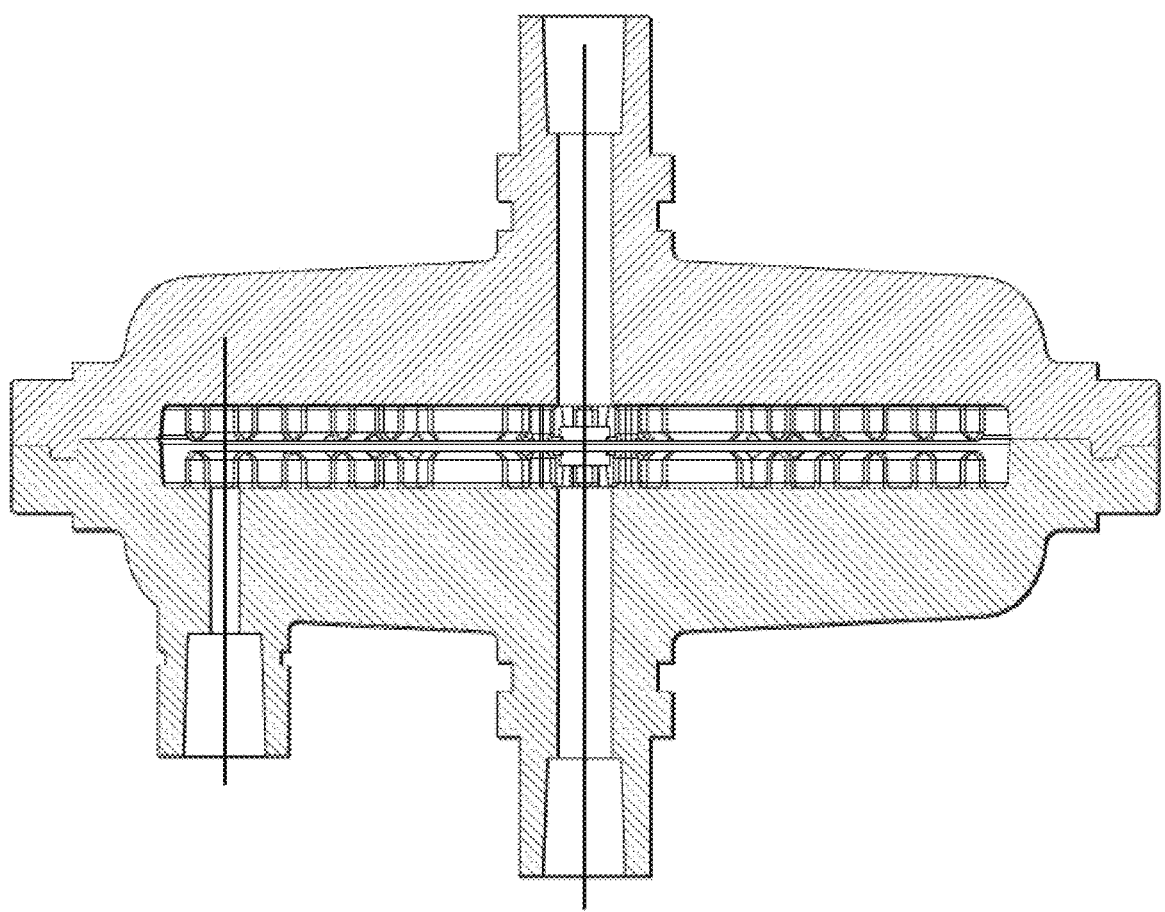
FIG. 12 depicts a cross-section of the disposable or semi-disposable housing for a 50 mm syringe column comprising a disk-shaped filtration membrane for lab-scale use.
Figure 13:
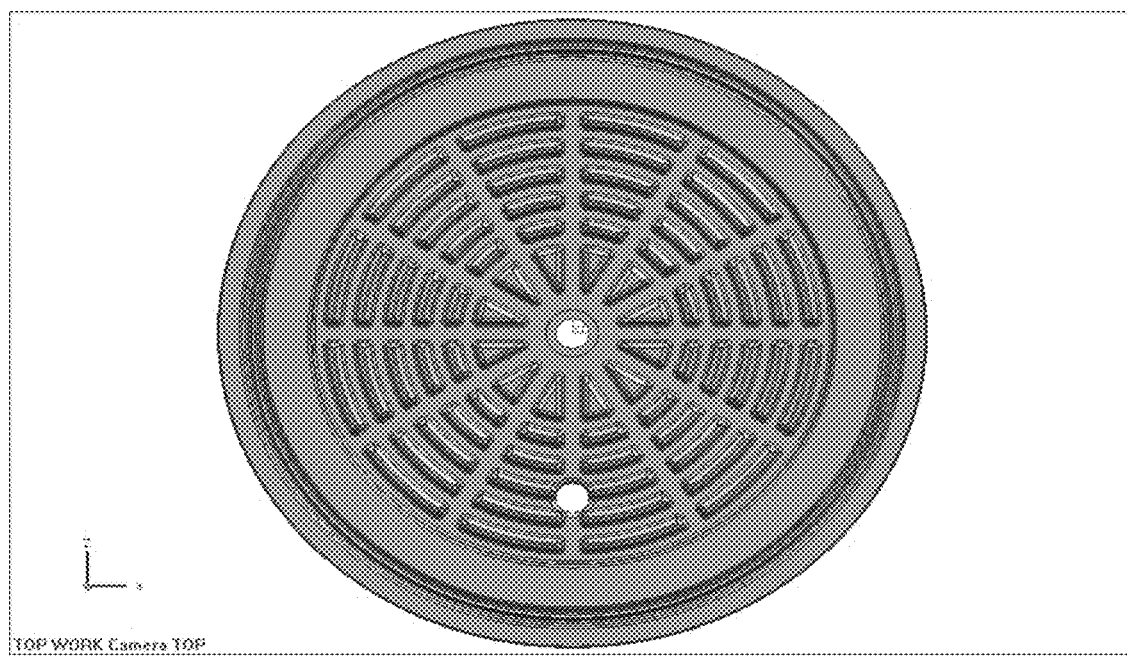
FIG. 13 depicts the drainage grid in the housing depicted in FIG. 12 for use with a 50 mm disk-shaped membrane.
Figure 14:
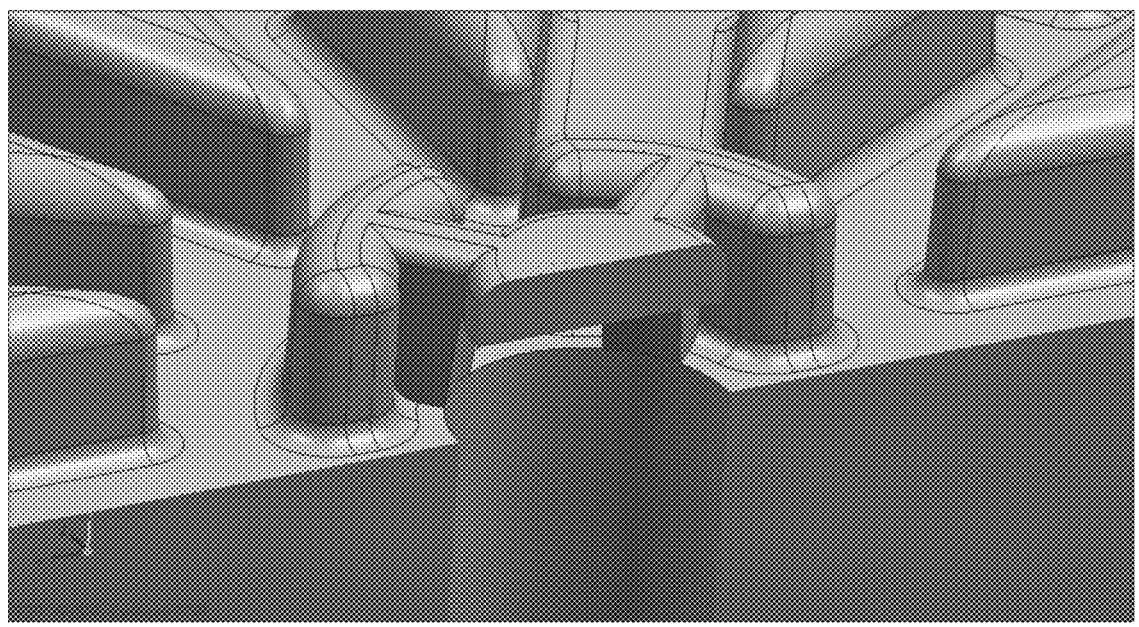
FIG. 14 depicts an inlet flow deflector in a reusable stainless steel housing for a 50 mm syringe column comprising a disk-shaped filtration membrane for lab-scale use.
Figure 15:
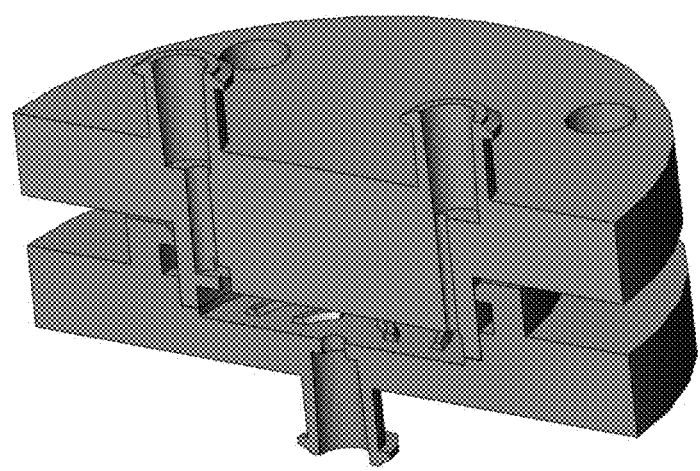
FIG. 15 depicts a stainless steel holder for use as a reusable housing for a 25 mm disk-shaped membrane for lab-scale use.
Figure 16:
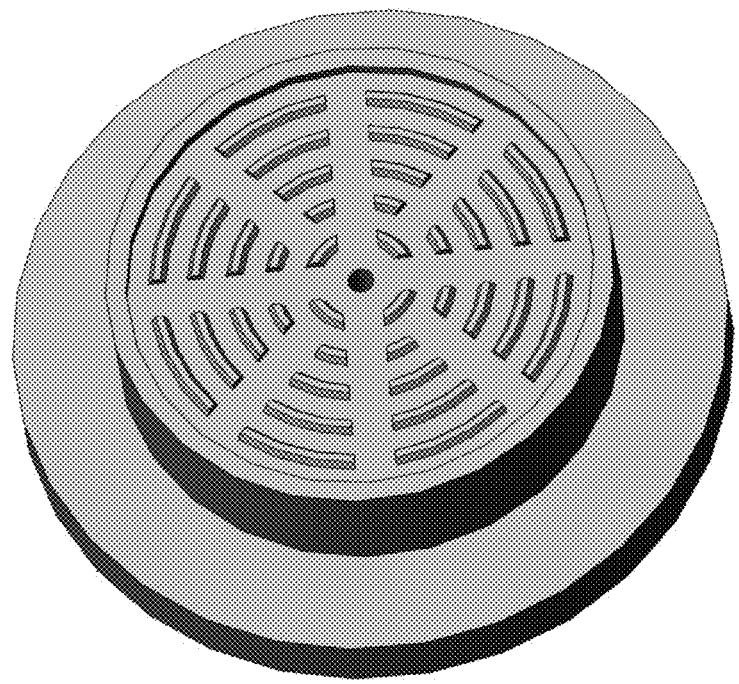
FIG. 16 depicts a component of a reusable stainless steel housing for lab-scale syringe columns.
Figure 17:
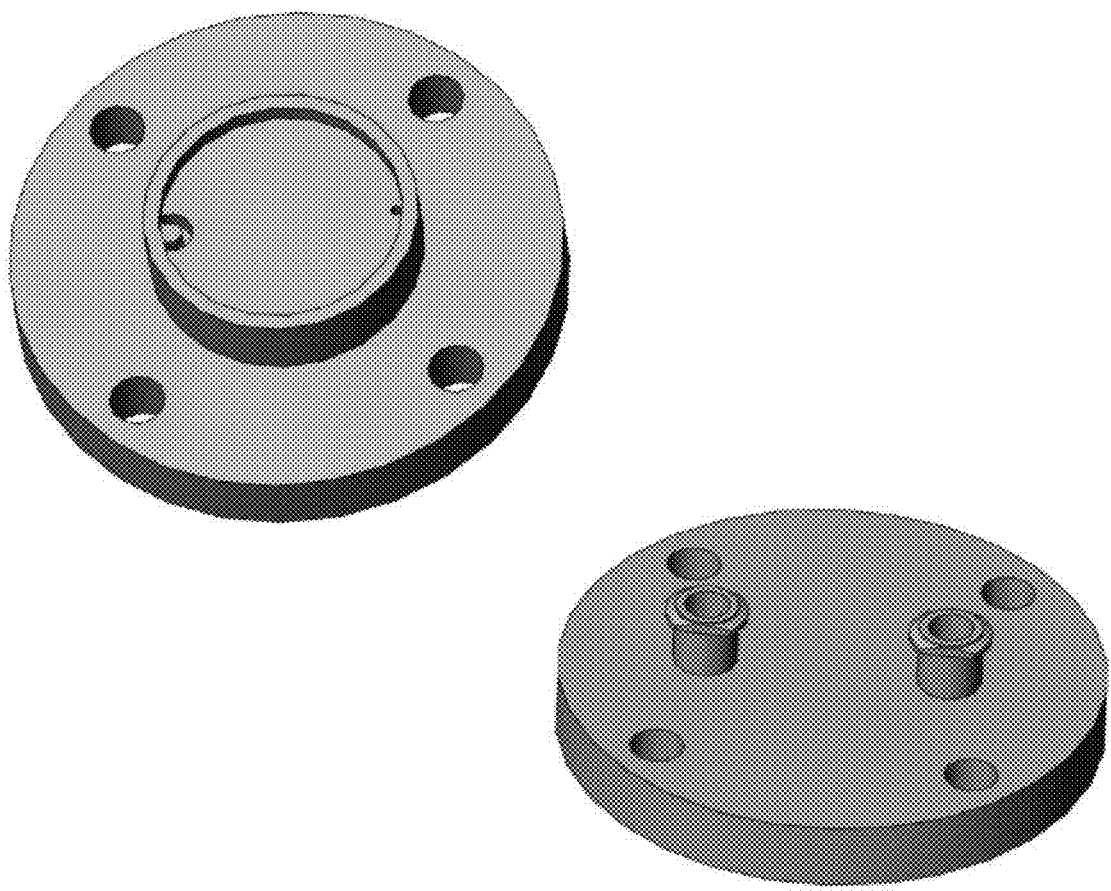
FIG. 17 depicts two components of a reusable stainless steel housing for lab-scale syringe columns.
Figure 18:
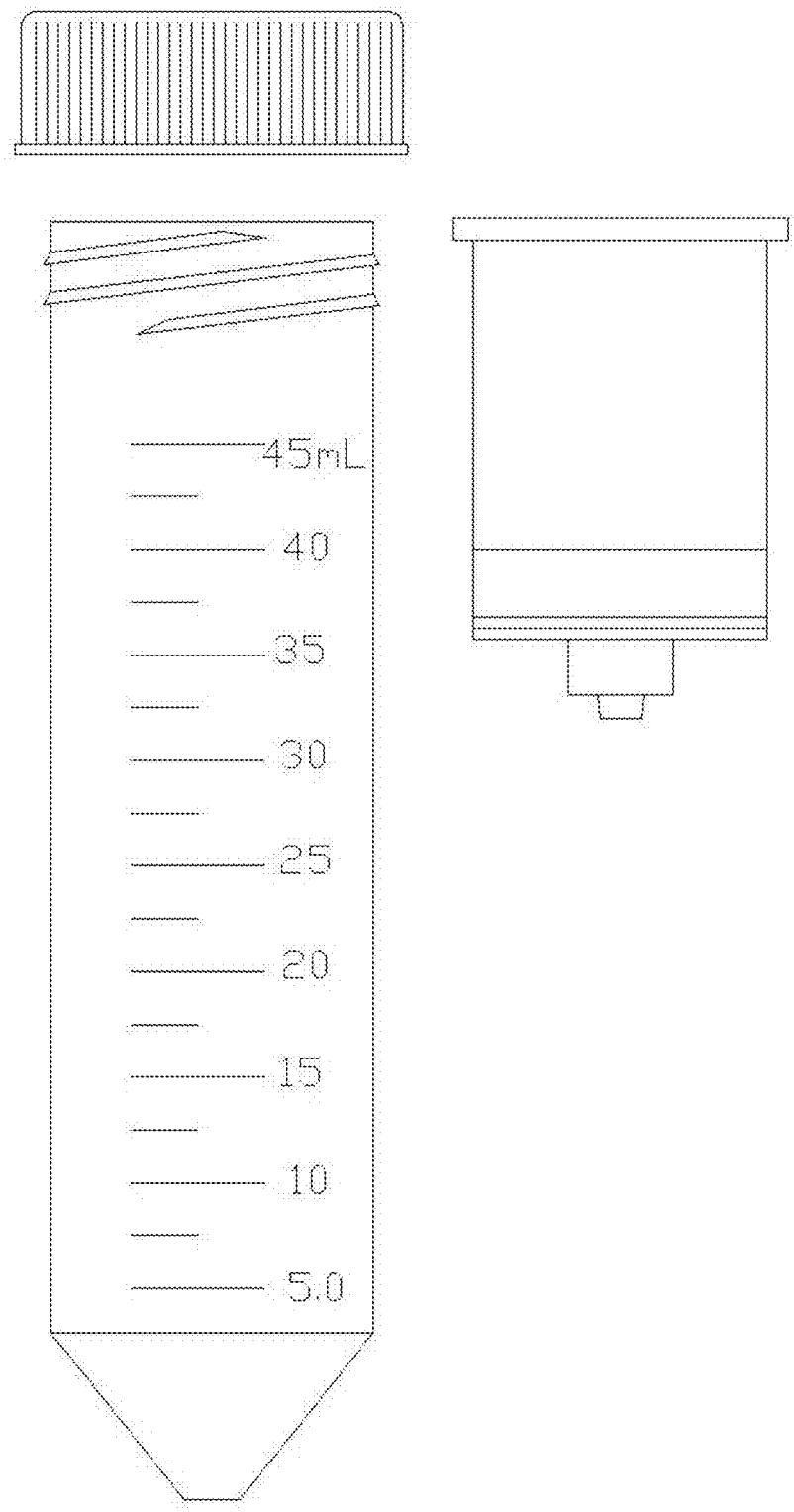
FIG. 18 depicts a maxi spin column (left), and a device for supporting a cut disk membrane within the column (right).
Figure 19:
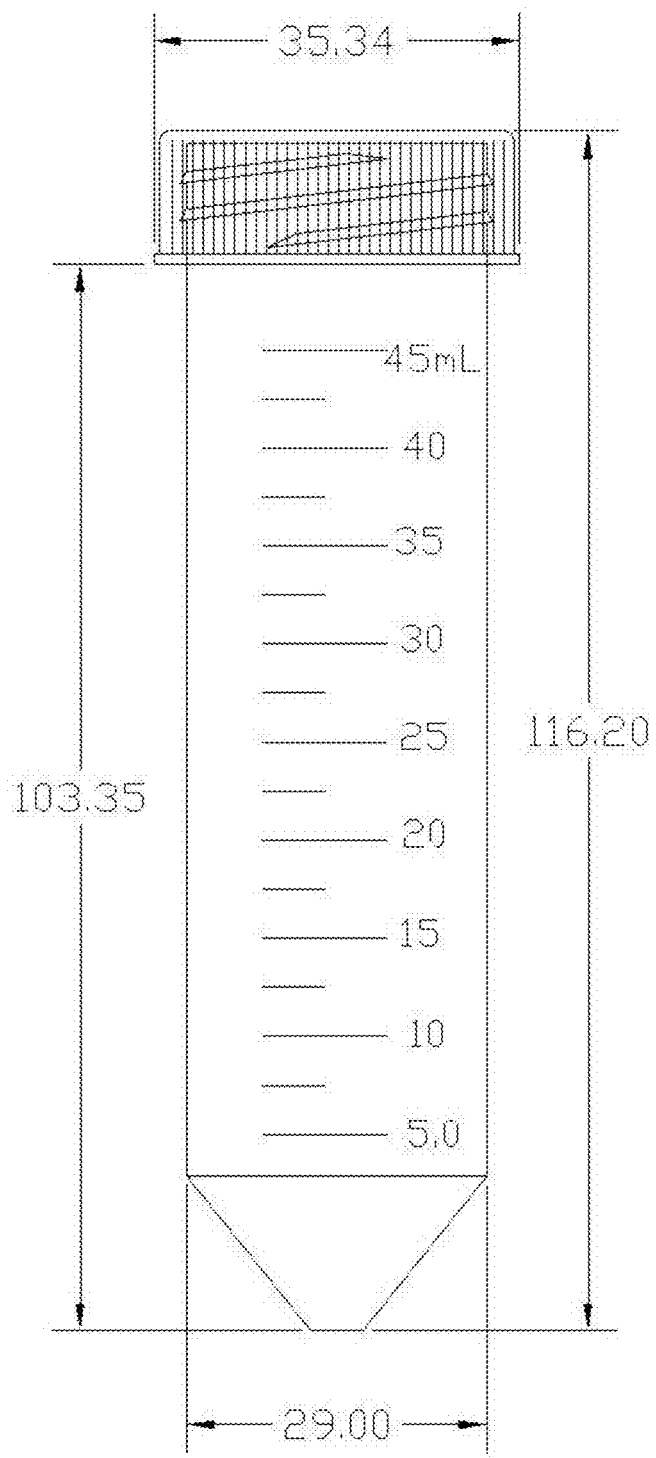
FIG. 19 depicts the dimensions of a maxi spin column.
Figure 20:
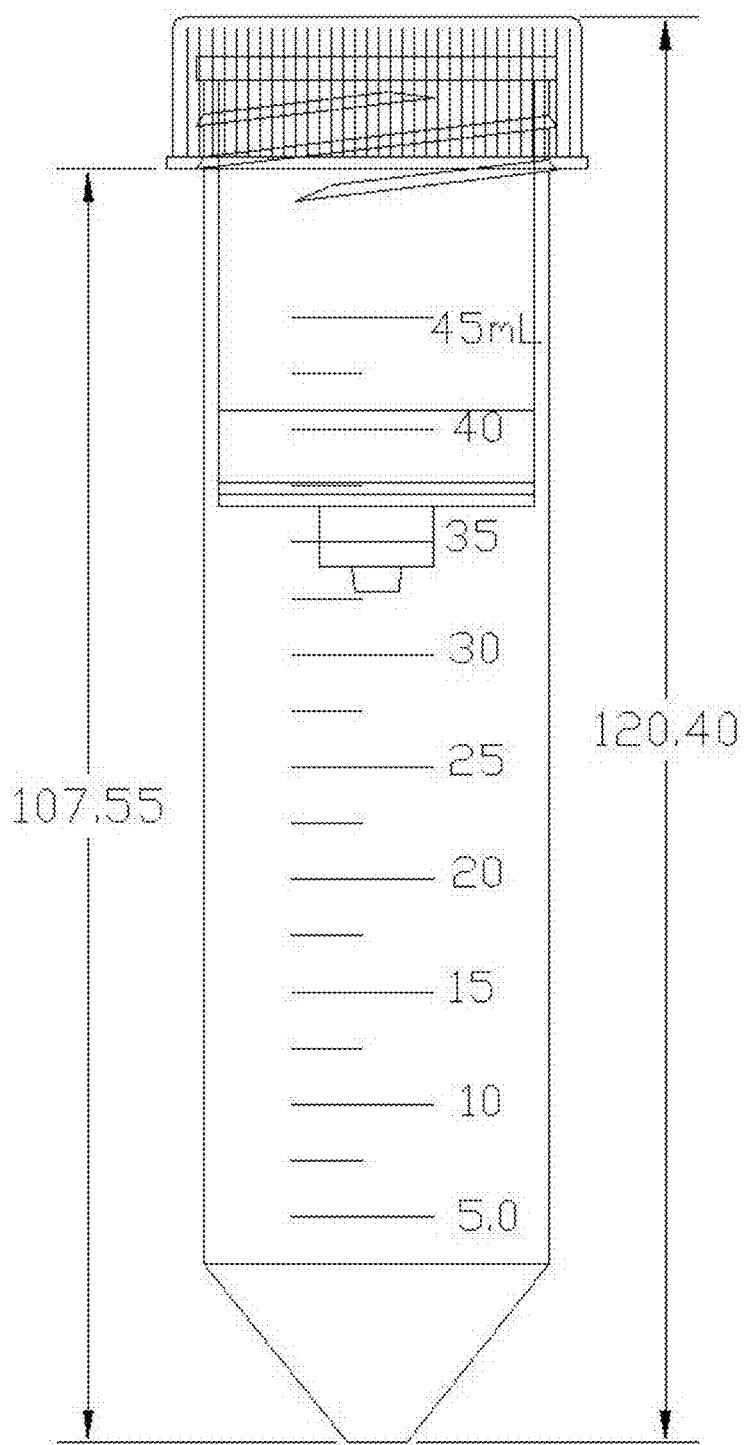
FIG. 20 depicts the dimensions of a maxi spin column with a device for supporting a cut disk membrane within the column.
Figure 21:
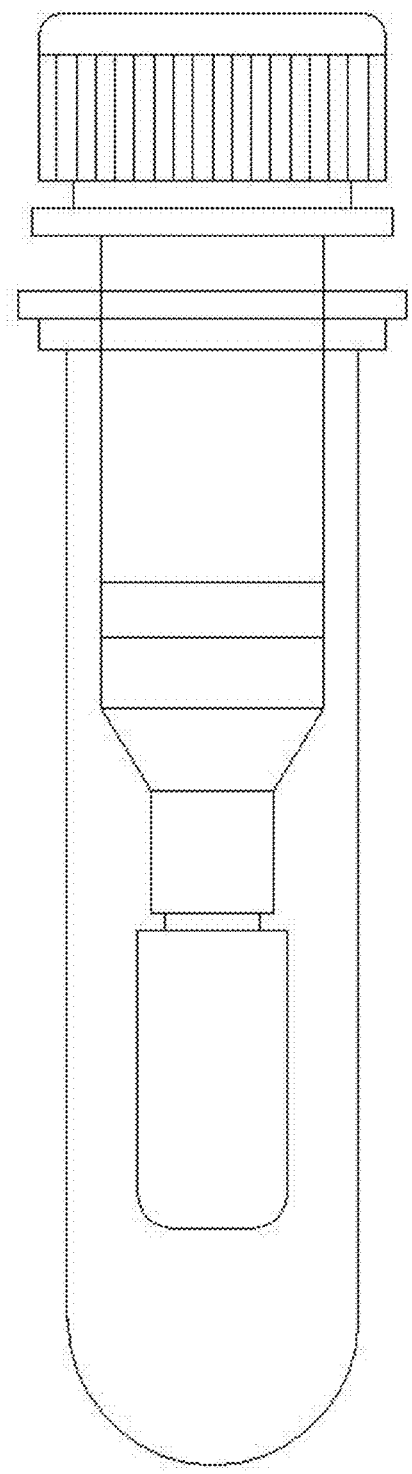
FIG. 21 depicts a mini spin column with a device for supporting a cut disk membrane within the column.
Figure 22:
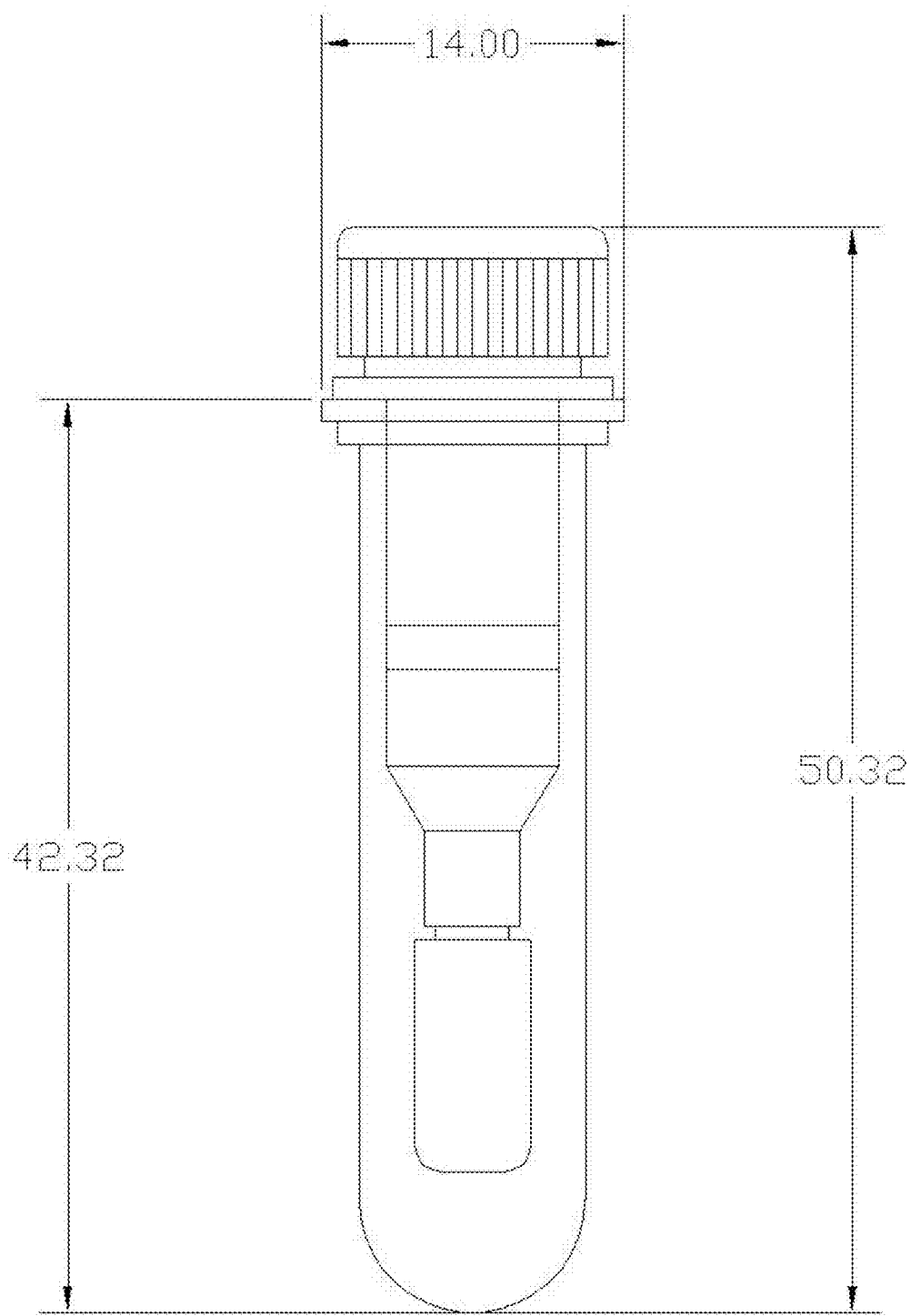
FIG. 22 depicts the dimensions of a mini spin column with a device for supporting a cut disk membrane within the column.

The height of the feed channel may impact the ability to maximize the amount of adsorbed target molecule. Smaller feed channel heights may induce greater shear or turbulence at the membrane surface, which either inhibits adsorption or removes target material that does deposit. The channel height needs to be at least 10 mm and more ideally >20 mm, typically 23 mm (FIG. 7).

Screen changes have not been identified as a driver for performance in cassette design.

EXAMPLE 6

Device Design: Spiral

Figure 23:
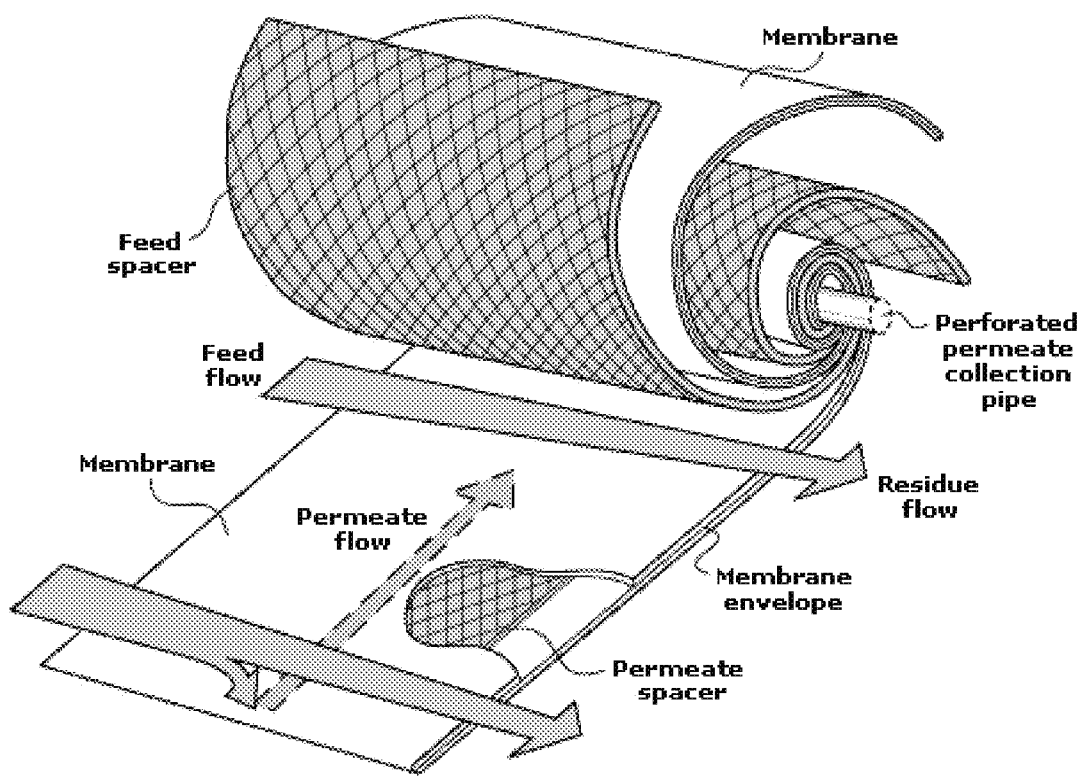
FIG. 23 depicts an exemplary configuration of a spiral wound device. There are three series of concentric envelopes, wherein each envelope has a spacer material inside and three of the sides are sealed. Each envelope is separated by a feed spacer. Fluid flow is directed such that raw fluid travels on the outside of each envelope and is forced through the membrane. The permeate travels along the permeate spacer to the permeate collection pipe.

FIG. 23 depicts a spiral wound device. When membranes of the current invention are incorporated into this device, highly contaminated or very viscous feed streams can be effectively separated into their desired parts.

EXAMPLE 7

Antibody Purification: Membrane functionalized with Protein A

A 0.01 SQM Protein A cassette with an open channel, suspended screen design which enabled a fluid flow tangential to the plane of the membrane was evaluated using an un-clarified feed stream which contained the monoclonal antibody (mAb) target. Traditional resin chromatographic separation processes cannot process un-clarified feed streams. The only method that had been demonstrated able to capture the mAb target on bench scale was an expanded bed column functioning in batch mode with a static soak. This modified expanded bed was uneconomical and impractical at larger scale. On the other hand, the cassettes were effective in capturing the target MAb product when used a simple flow through mode. This mode allowed the process stream to flow across the membrane such that debris in the fluid did not blind the membrane. Binding of the target species in this mode was a surface effect only.

Lysis Procedure: 270 g mAb 4420 pellet diluted 1 part pellet, 3 parts 10× phosphate buffer solution (PBS), 1 part 5× Pfenix lysis buffer. Homogenized for 5 minutes, and sonicated for 10 minutes. Loaded onto the membrane as an un-clarified and undiluted feed stream.

Membrane Procedure: A membrane cassette with an active surface area of 0.01 m$^2$ and pore size of 0.3 μm was equilibrated in PBS at pH 7.4. This device was then loaded by complete system recirculation with lysed mAb 4420 for one hour. The device was then washed with 1 L of 1× PBS pH 7.4, and eluted using a 10 minute recirculation of 0.1 M Glycine at pH 2.9 followed by 100 mL system flush with 0.1 M Glycine pH 2.9. The feed was run in flow through mode at 100 mL/min with permeate shut off which limited the device to surface binding only from the un-clarified lysate. A gel electrophoresis qualitative analysis indicated that significant amounts of mAb had been captured.

Conclusion: The cross-flow product provided a simple, on-off bind-elute capture process that could capture and concentrate intact mAb (observed binding was in the range of 5-10 mg/mL) as well as a lot of contaminants. With development, membrane could serve as a scalable capture method for un-clarified mAb Pseudomonas feed streams.

EXAMPLE 8

His-Tagged Protein Purification: Membrane Functionalized with IMAC Ni

A 0.02 SQM IMAC-Ni (iminodiacetic acid complexed to Ni) cassette with an open channel, suspended screen design which enabled a fluid flow tangential to the plane of the membrane was evaluated using a feed stream containing a his-tagged protein target. Traditional resin-based chromatographic separation processes cannot process un-clarified feed streams. In this experiment, the cassettes were effective in capturing the target product in a simple flow through mode. This mode allowed the process stream to flow across the membrane such that debris in the fluid did not blind the membrane. Binding of the target species in this mode was a surface effect only. The product was able to be run with multiple cycles with no loss in binding capacity.

Lysis Procedure: 8 L of cell harvest material was diluted with 2 L of 5× Pfenix Lysis Buffer. This mixture was allowed to mix for 2 hours until the material had liquefied.

Membrane Procedure: A membrane cassette with an active surface area of 0.02 m$^2$ was equilibrated in 50 mM PBS, 500 mM NaCl, 5% (wt) glycerol and 25 mM Imidazole at pH 8.0. The cassette was then run with the liquefied cell harvest material at a 100 mL/min feed rate with no permeate flow. This was flowed by elution using 500 mL 1× PBS, 500 mM Imidazole at pH 7.4. This process was repeated 3 times in sequence with the follow details:

Run 1: 1 L of Lysate was centrifuged and diluted by a factor of 5 in equilibration buffer. The device was then loaded by complete system recirculation for 1 hour time and material was able to permeate through the pores at 20 PSIg inlet pressure. A gel electrophoresis qualitative analysis indicated that significant amounts his-tagged protein had been captured.

Run 2: 1 L of Lysate was only centrifuged prior to use. The device was then loaded by complete system recirculation for 1 hour time and material was able to permeate through the pores at 20 PSIg inlet pressure. A gel electrophoresis qualitative analysis indicated that significant amounts his-tagged protein had been captured Run 3: 1 L of Lysate was used without pre-treatment. The device was then loaded by complete system recirculation for 15, 30, 45, 60 minute load times. The device was eluted after each cycle and the membrane not stripped (cleaned) between elutions. When the permeate line was closed, no back pressure increase to system was observed during load indicating that the membrane had not blinded.

Conclusion: The IMAC-Ni product yielded excellent purification characteristics (observed binding was in the range of 60-80 mg/mL) without optimization. Despite manufacturers designation as "single-use," 7× reuse demonstrated for IMAC membrane without the need for EDTA strip and re-charge.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A fluid treatment device comprising:
a housing unit, wherein the housing unit comprises:
(a) an inlet, a retentate outlet, and a permeate outlet;
(b) a fluid flow path between the inlet and the retentate outlet; and
(c) a composite material within the housing unit, wherein the composite material comprises:
a support member comprising a plurality of pores extending through the support member; and
a non-self-supporting macroporous cross-linked gel comprising macropores having an average size of 10 nm to 3000 nm, said macroporous gel being located in the pores of the support member;
wherein:
the macroporous cross-linked gel is selected from the group consisting of N,N'-methylenebisacrylamide cross-linked copolymers and cross-linked poly- mers of isopropylacrylamide, dodecyl acrylate, ethyl acrylate, ethylene oxide, hydroxymethyl acrylate, n-butyl acrylate, N-(hydroxymethyl) acrylamide, N-methacryloylacrylamide, N-methyl-N-vinylacetamide, N,N-dimethylacrylamide, N-vinyl-pyrrolidone, octadecylacrylamide, octyl acrylate, propyl acrylate, stearyl acrylate, styrene, or vinyl alcohol, or a mixture thereof;

the cross-linked gel comprises functional groups, wherein said functional groups are Protein A;

said macropores of said macroporous cross-linked gel are smaller than said pores of said support member; and the pores of the support member are substantially perpendicular to the fluid flow path from the inlet to the retentate outlet, and said fluid flow path from the inlet to the retentate outlet is substantially parallel to the surface of a filter medium comprising the composite material.

2. The fluid treatment device of claim 1, wherein the composite material is arranged in a substantially coplanar stack of substantially coextensive sheets, a substantially tubular configuration, or a substantially spiral wound configuration.

3. The fluid treatment device of claim 1, wherein
the support member is in the form of hollow porous fibers;
each hollow porous fiber defines a lumen;
the lumen is from about 20 μm to about 100 μm in diameter; and
the lumen is substantially perpendicular to the pores in the hollow porous fiber support member.

4. The fluid treatment device of claim 3, wherein a plurality of hollow porous fibers are arranged in a bundle.

5. The fluid treatment device of claim 1, wherein the housing unit is substantially cylindrical.

6. The fluid treatment device of claim 1, wherein the housing unit is disposable or reusable.

7. The fluid treatment device of claim 1, wherein the housing unit is plastic or stainless steel.

8. The fluid treatment device of claim 1, wherein the inlet, the retentate outlet, or the permeate outlet is a press fit attachment point, a luer lock attachment point, or a hose barb attachment point.

9. The fluid treatment device of claim 1, wherein the macroporous crosslinked gel is cross-linked by N,N'-methylenebisacrylamide or a polyfunctional macromonomer.

10. The fluid treatment device of claim 1, wherein the support member consists essentially of polymeric material in the form of a membrane that has a thickness of from about 10 μm to about 500 μm and comprises pores of average size between about 0.1 to about 25 μm.

11. The fluid treatment device of claim 1, wherein the support member consists essentially of a polyolefin.

12. The fluid treatment device of claim 1, wherein the composite material has 2 to 10 separate support members.

13. The fluid treatment device of claim 1, wherein the composite material is a pleated membrane.

14. The fluid treatment device of claim 1, wherein the support member comprises a polymeric material selected from the group consisting of polysulfones, polyethersulfones, polyphenyleneoxides, polycarbonates, polyesters, cellulose and cellulose derivatives.

* * * * *